United States Patent
Ramkhelawan et al.

(10) Patent No.: US 9,339,338 B2
(45) Date of Patent: May 17, 2016

(54) ADJUSTABLE SURGICAL INSTRUMENT STRINGER WITH PEGS, TRAY SYSTEM, AND METHOD OF STERILIZATION

(71) Applicant: Restore Medical Solutions, Inc., Memphis, TN (US)

(72) Inventors: Ryan Ramkhelawan, Collierville, TN (US); Shawn Flynn, Memphis, TN (US)

(73) Assignee: Restore Medical Solutions, Inc., Memphis, TN (US)

( * ) Notice: Subject to any disclaimer, the term of this patent is extended or adjusted under 35 U.S.C. 154(b) by 0 days.

(21) Appl. No.: 14/847,648

(22) Filed: Sep. 8, 2015

(65) Prior Publication Data
US 2015/0374439 A1 Dec. 31, 2015

Related U.S. Application Data

(60) Division of application No. 13/761,986, filed on Feb. 7, 2013, now Pat. No. 9,156,571, which is a continuation-in-part of application No. 13/570,236, filed on Aug. 8, 2012, which is a continuation-in-part of application No. 13/284,099, filed on Oct. 28, 2011, now abandoned.

(51) Int. Cl.
| | | |
|---|---|---|
| *A61B 19/02* | (2006.01) | |
| *B65B 5/08* | (2006.01) | |
| *A61L 2/26* | (2006.01) | |

(52) U.S. Cl.
CPC .......... *A61B 19/0256* (2013.01); *A61B 19/026* (2013.01); *A61B 19/0271* (2013.01); *B65B 5/08* (2013.01); *A61B 2019/0213* (2013.01); *A61B 2019/0258* (2013.01); *A61B 2019/0272* (2013.01); *A61B 2019/0281* (2013.01); *A61L 2/26* (2013.01); *A61L 2202/24* (2013.01)

(58) Field of Classification Search
CPC .......... A61B 19/0256; A61B 19/0271; A61B 2019/0231; A61L 2202/17; A61L 2202/123; B65B 5/08
USPC .............. 211/85.13, 70.6, 70.7, 126.1, 133.6; 206/363, 368, 369, 375; 422/300, 301
See application file for complete search history.

(56) References Cited

U.S. PATENT DOCUMENTS

| | | | | |
|---|---|---|---|---|
| 3,925,014 A | * | 12/1975 | Langdon ................... | A61L 2/26 206/370 |
| 4,043,754 A | * | 8/1977 | Sklar ......................... | A61L 2/26 206/370 |
| 4,229,420 A | * | 10/1980 | Smith ................ | A61B 19/0256 206/363 |
| 4,342,391 A | * | 8/1982 | Schainholz ........ | A61B 19/0256 206/370 |
| 4,512,466 A | * | 4/1985 | Delang .............. | A61B 19/0256 206/370 |
| 4,577,755 A | * | 3/1986 | Ramsay ............. | A61B 19/0256 206/370 |
| 4,865,821 A | * | 9/1989 | Langdon ............ | A61B 19/0256 206/370 |
| 4,911,297 A | * | 3/1990 | Suburu .................... | B25H 3/04 206/372 |
| 5,036,975 A | * | 8/1991 | Chow ....................... | B25H 3/04 206/372 |

(Continued)

*Primary Examiner* — Stanton L Krycinski
(74) *Attorney, Agent, or Firm* — Mathew L. Grell; Grell & Watson Patent Attorneys

(57) ABSTRACT

An adjustable stringer configured to string the ring handles of one or more surgical instruments, the stringer including two or more rod sections, wherein each rod section is configured to be inserted in one ring handle of the one or more surgical instruments, two or more angle sections, each angle section configured having one or more slidable connector sections, each slidable connector section configured to extend and retract along at least one of the two or more rod sections, and two or more releasable connectors, each releasable connector positioned between two of the two or more angle sections.

17 Claims, 19 Drawing Sheets

(56) References Cited

U.S. PATENT DOCUMENTS

| | | | | |
|---|---|---|---|---|
| 5,137,151 A * | 8/1992 | Choate | A61B 19/0256 | 206/370 |
| 5,449,069 A * | 9/1995 | Pijanowski | A61B 19/0256 | 206/370 |
| 5,451,380 A * | 9/1995 | Zinnanti | A61B 19/0256 | 206/370 |
| 5,505,916 A * | 4/1996 | Berry, Jr. | A61L 2/26 | 206/439 |
| 6,230,888 B1 * | 5/2001 | Frieze | A61B 19/0256 | 206/370 |
| 6,534,000 B1 * | 3/2003 | Michaelson | A61C 19/002 | 206/363 |
| 7,461,751 B2 * | 12/2008 | Lyons | A61B 19/0256 | 211/70.6 |
| 7,871,581 B1 * | 1/2011 | Coleman | A61L 2/26 | 206/210 |
| 8,567,880 B2 * | 10/2013 | Treat | A61B 19/02 | 206/363 |
| 8,641,984 B2 * | 2/2014 | Alston | A61B 19/0256 | 206/370 |
| 8,753,059 B2 * | 6/2014 | Baker | A61B 19/0256 | 211/85.13 |
| 2009/0152414 A1 * | 6/2009 | Lyons | A61B 19/0256 | 248/176.1 |
| 2012/0234781 A1 * | 9/2012 | Cogliano | B25H 3/06 | 211/85.13 |
| 2013/0074450 A1 * | 3/2013 | Higham | A61B 19/025 | 53/425 |

* cited by examiner

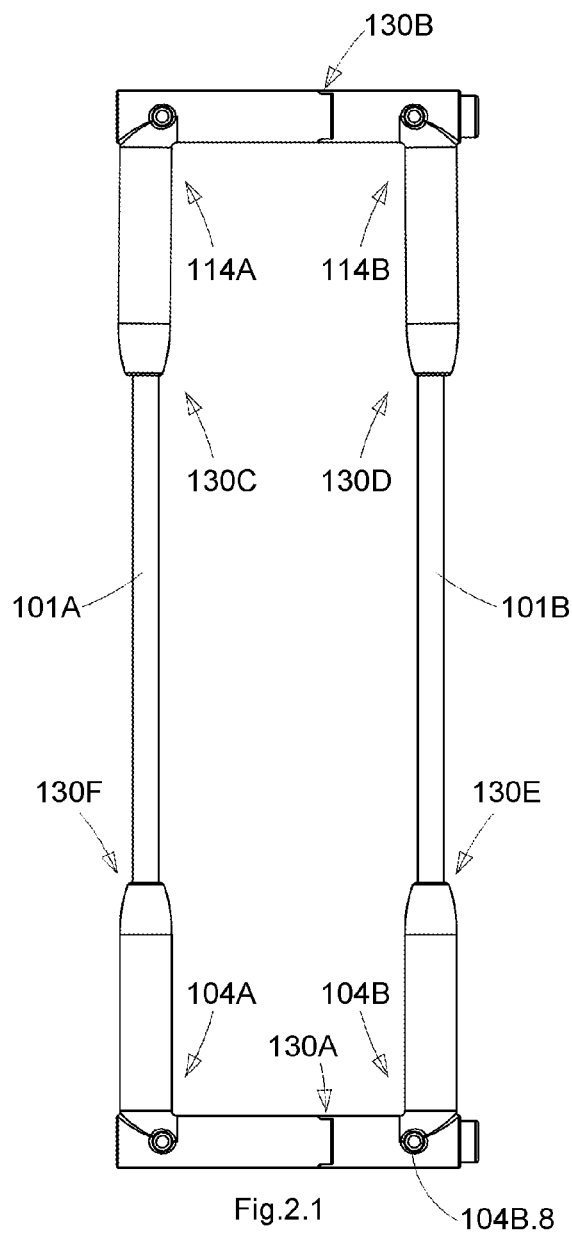
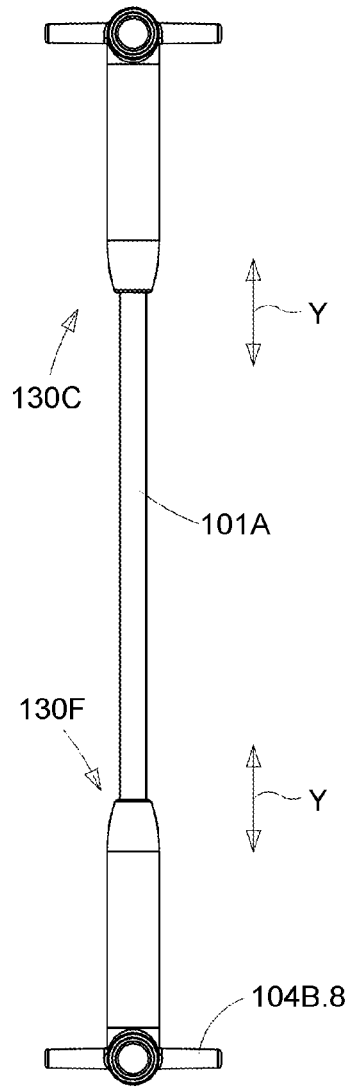
Fig.2.1
Fig.2.2
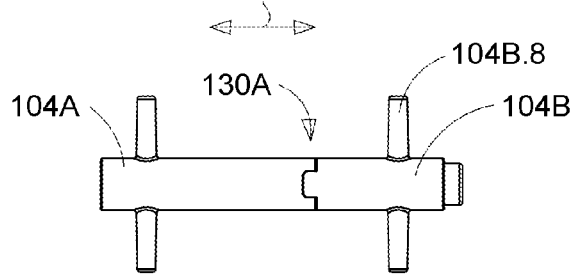
Fig.2.3
Fig.2

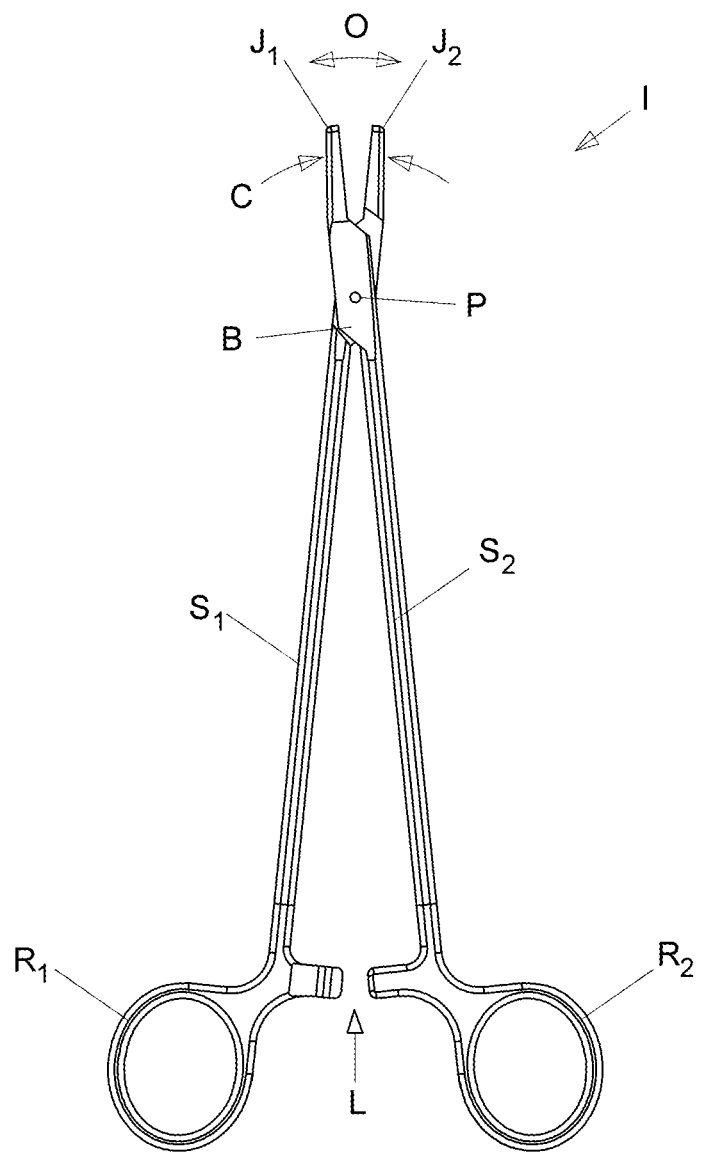
Fig. 4.1

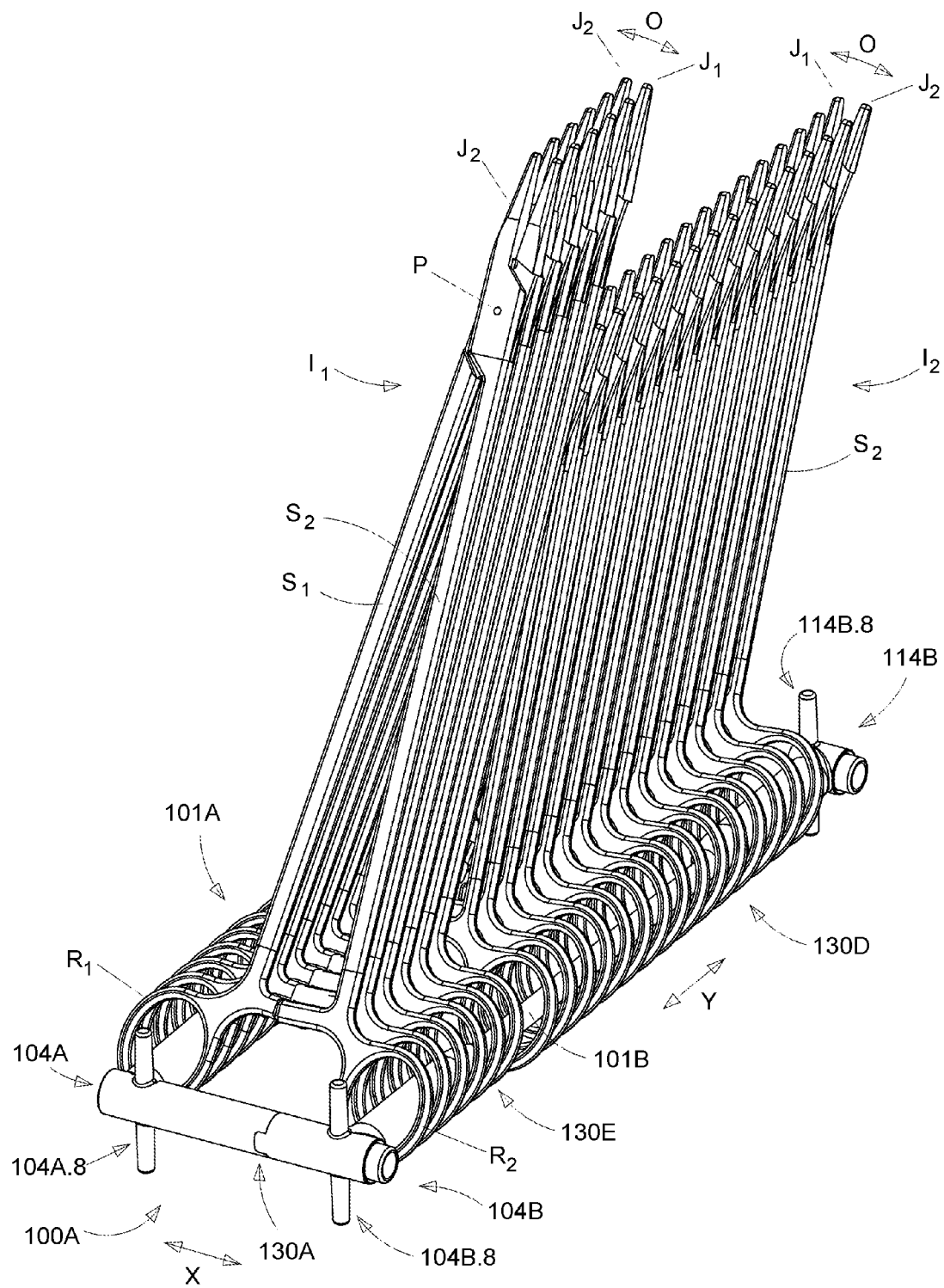
Fig.4.2

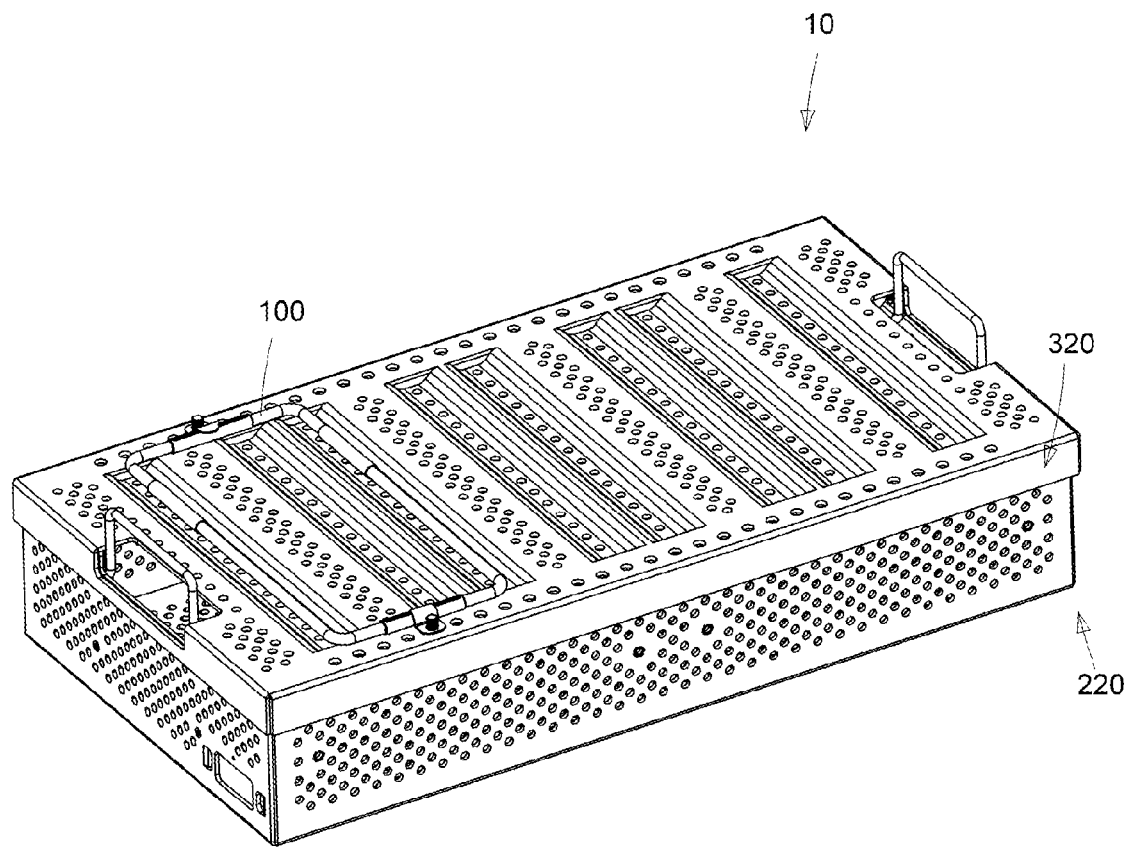
Fig. 5.1

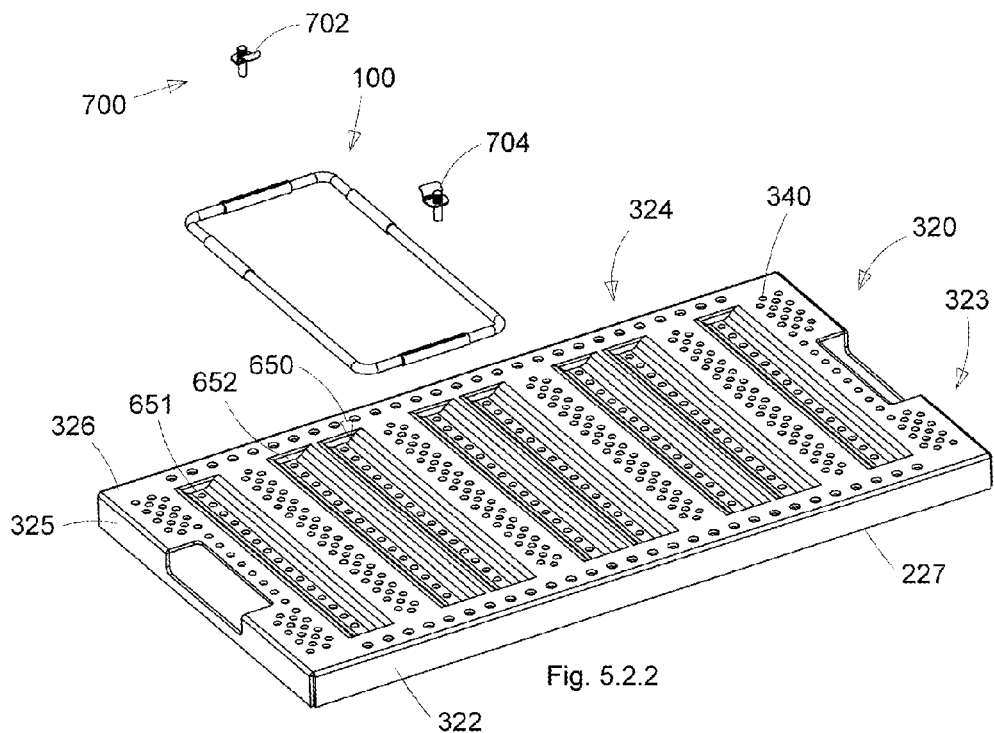
Fig. 5.2.2
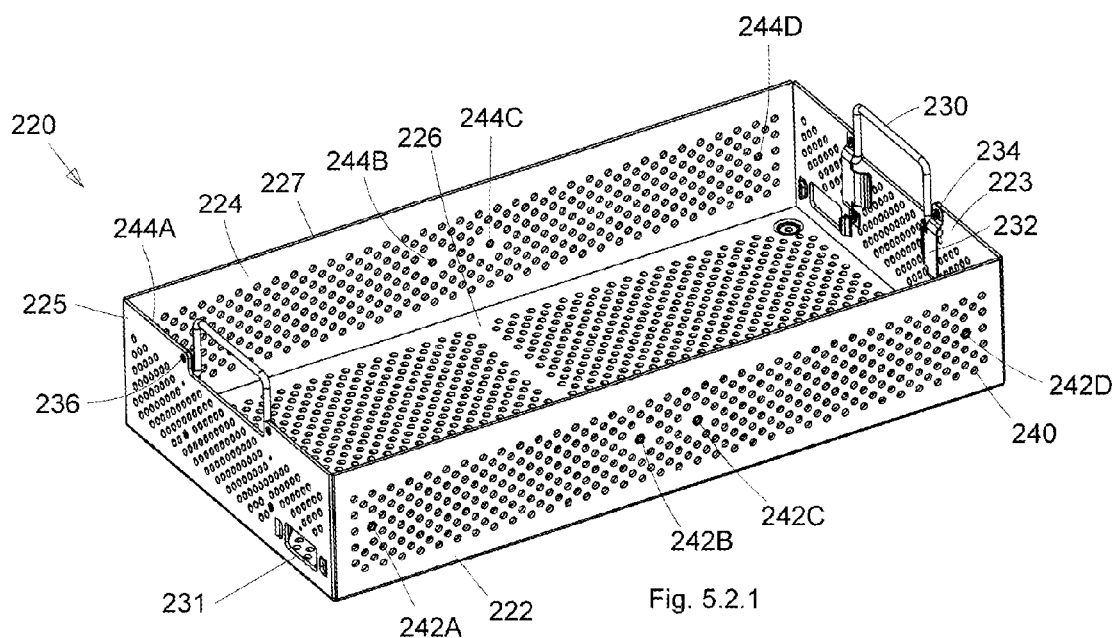
Fig. 5.2.1
Fig. 5.2

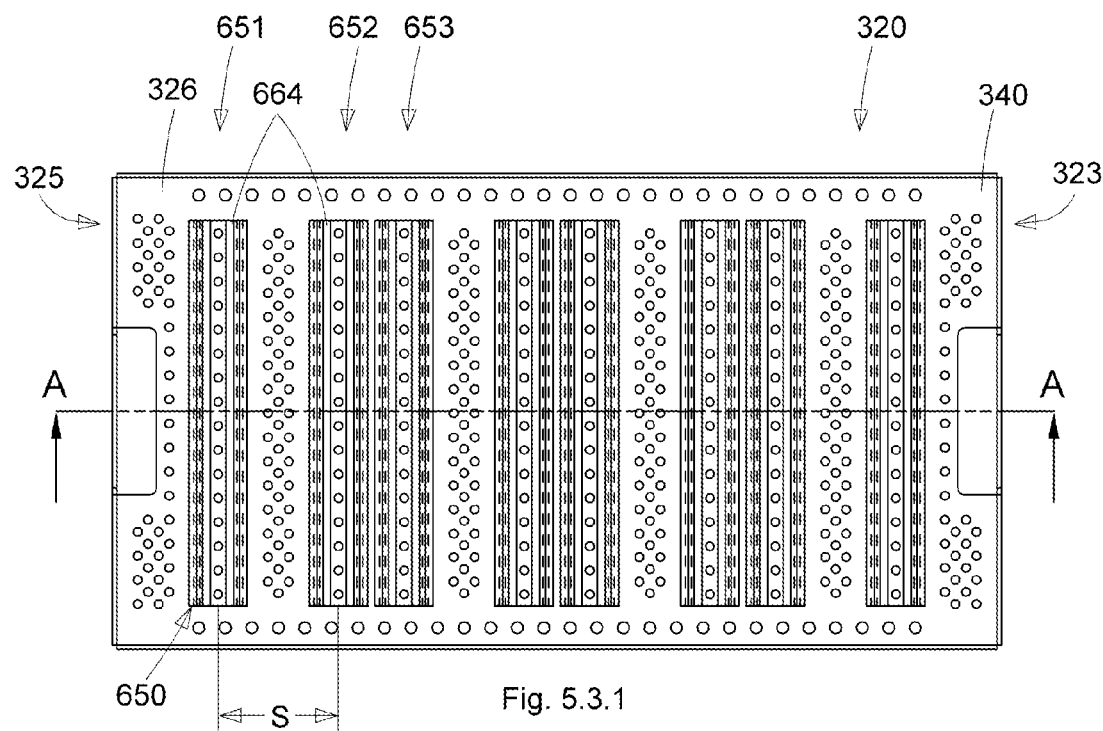
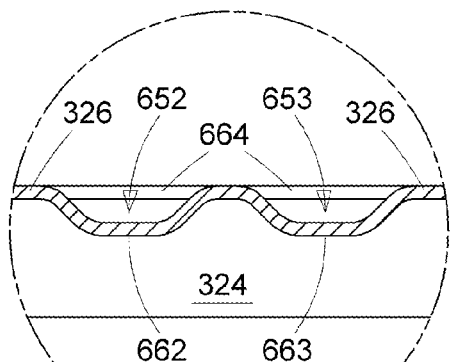
Fig. 5.3.2
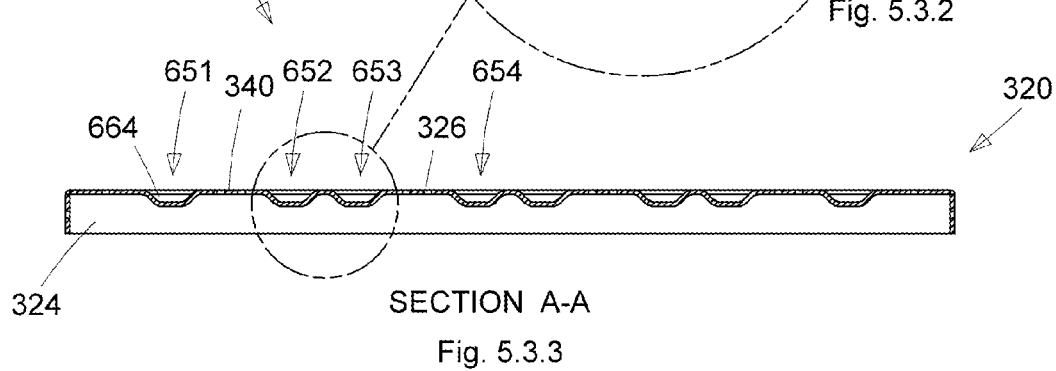
SECTION A-A
Fig. 5.3.3
Fig. 5.3

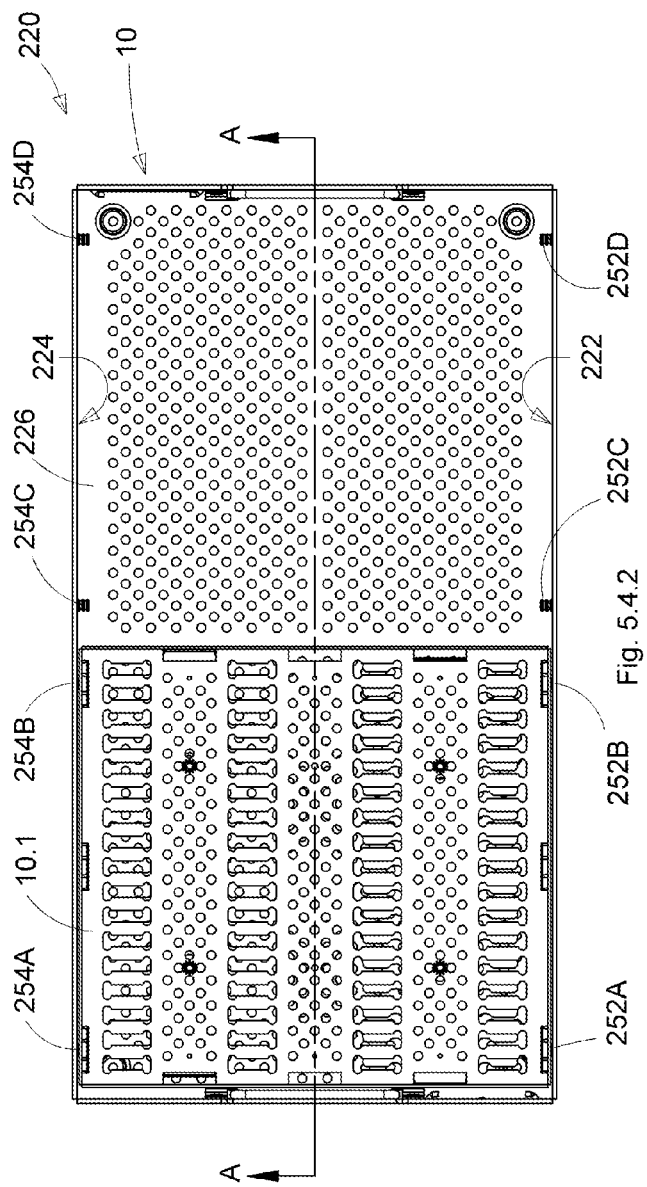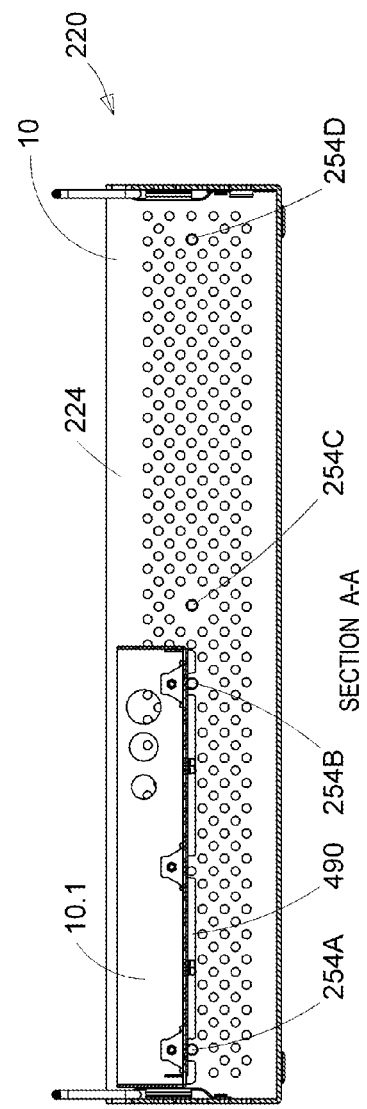
Fig. 5.4.2
Fig. 5.4.1
SECTION A-A

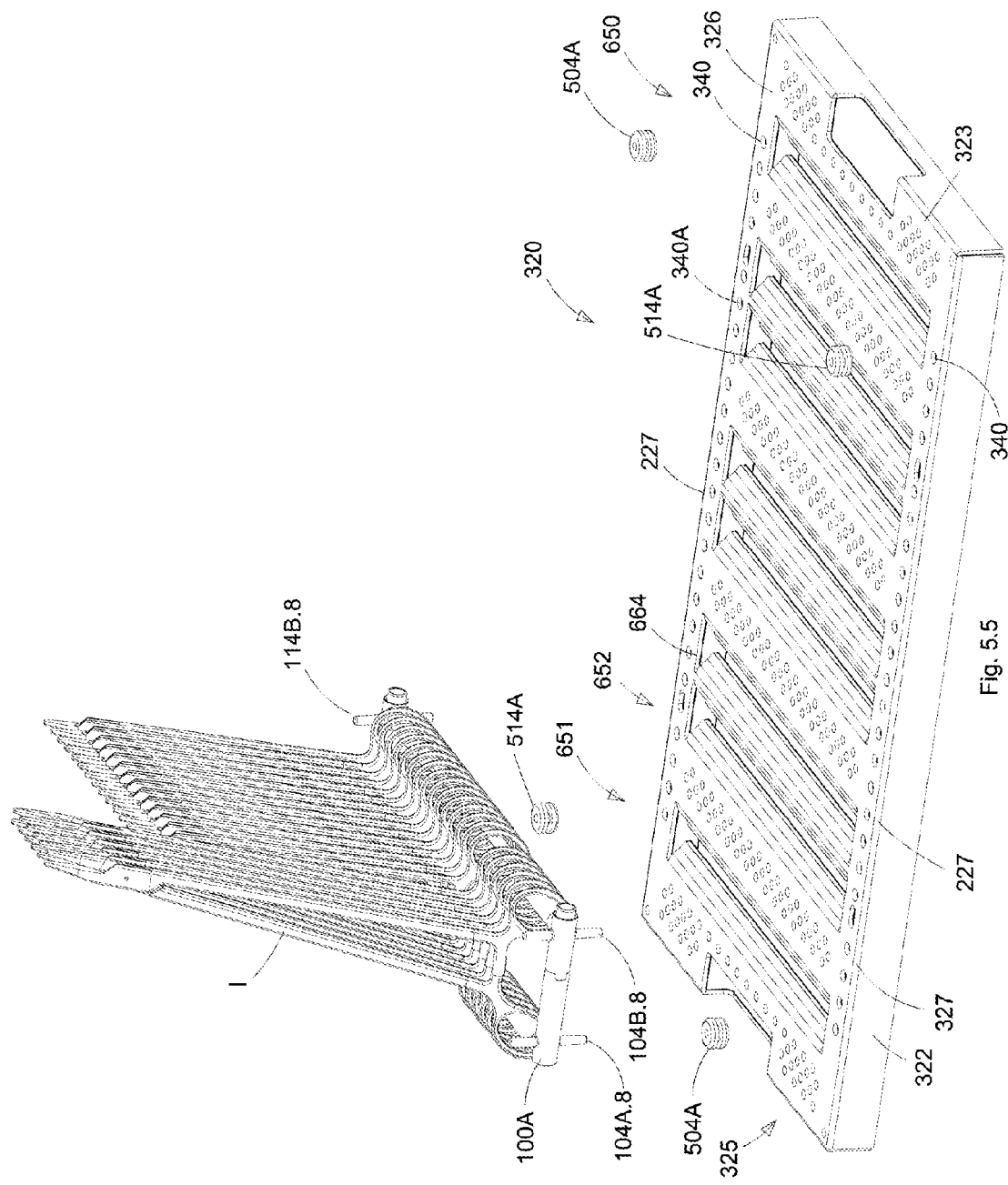

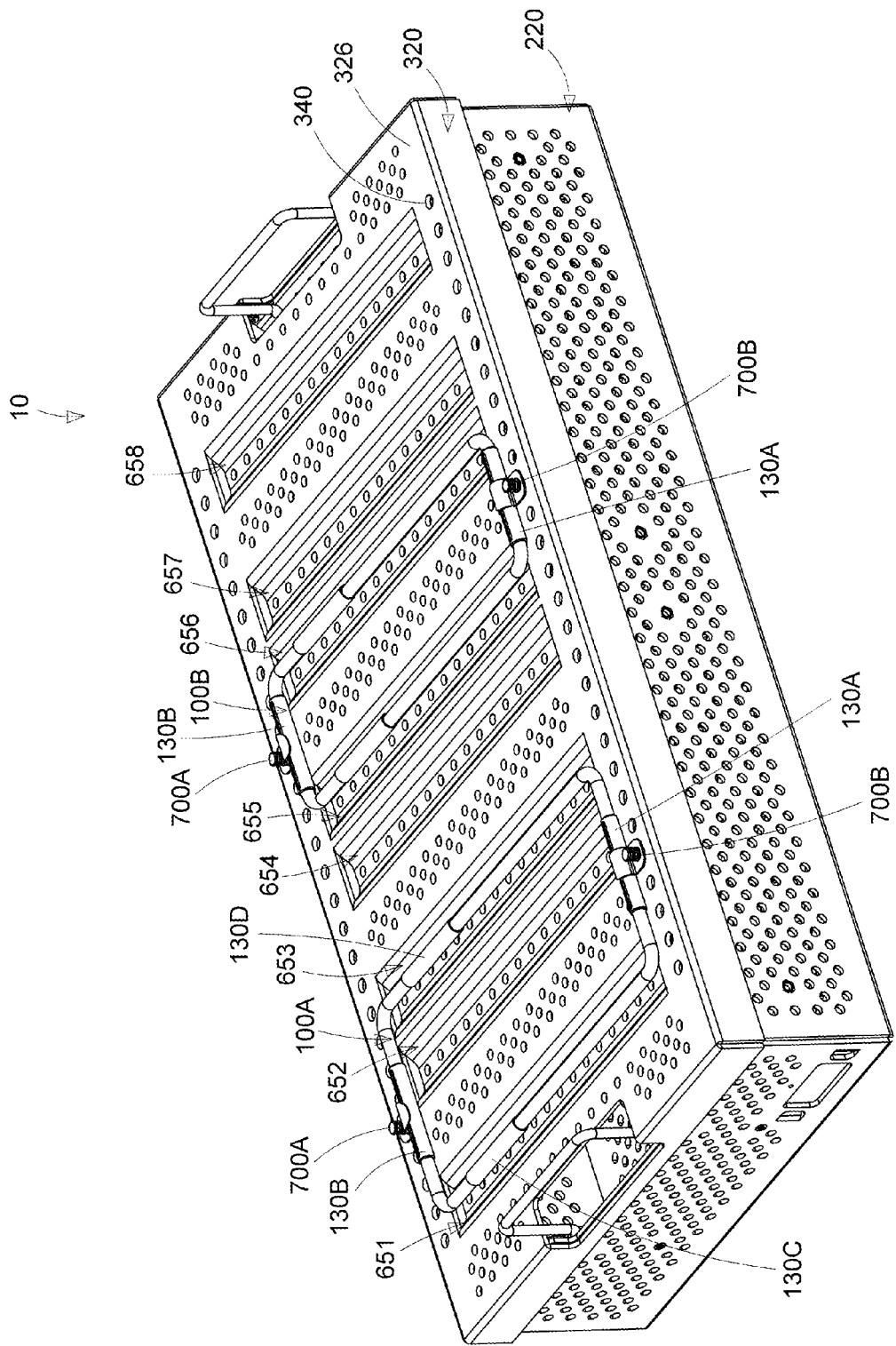
Fig. 6.1

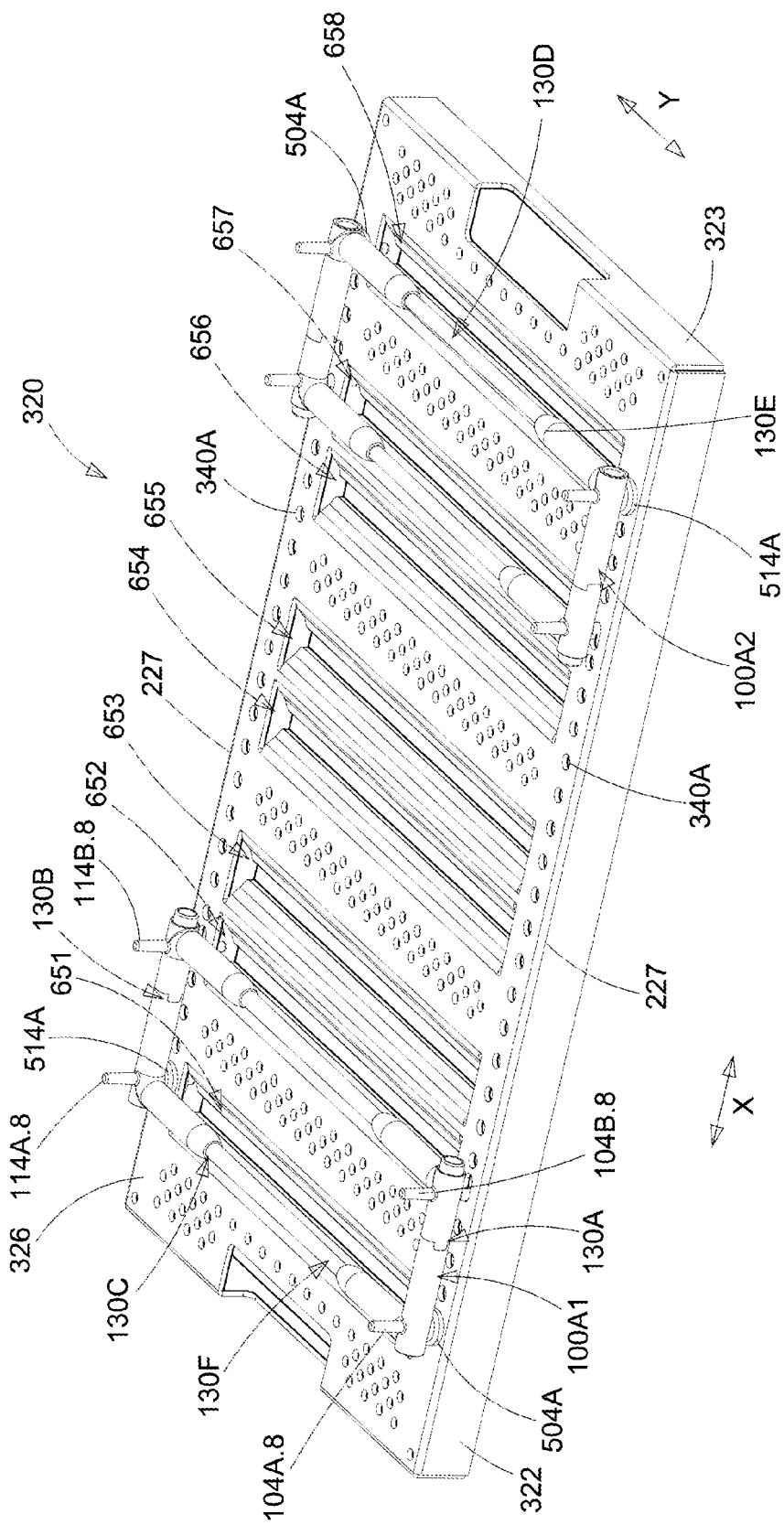
Fig. 6.1A

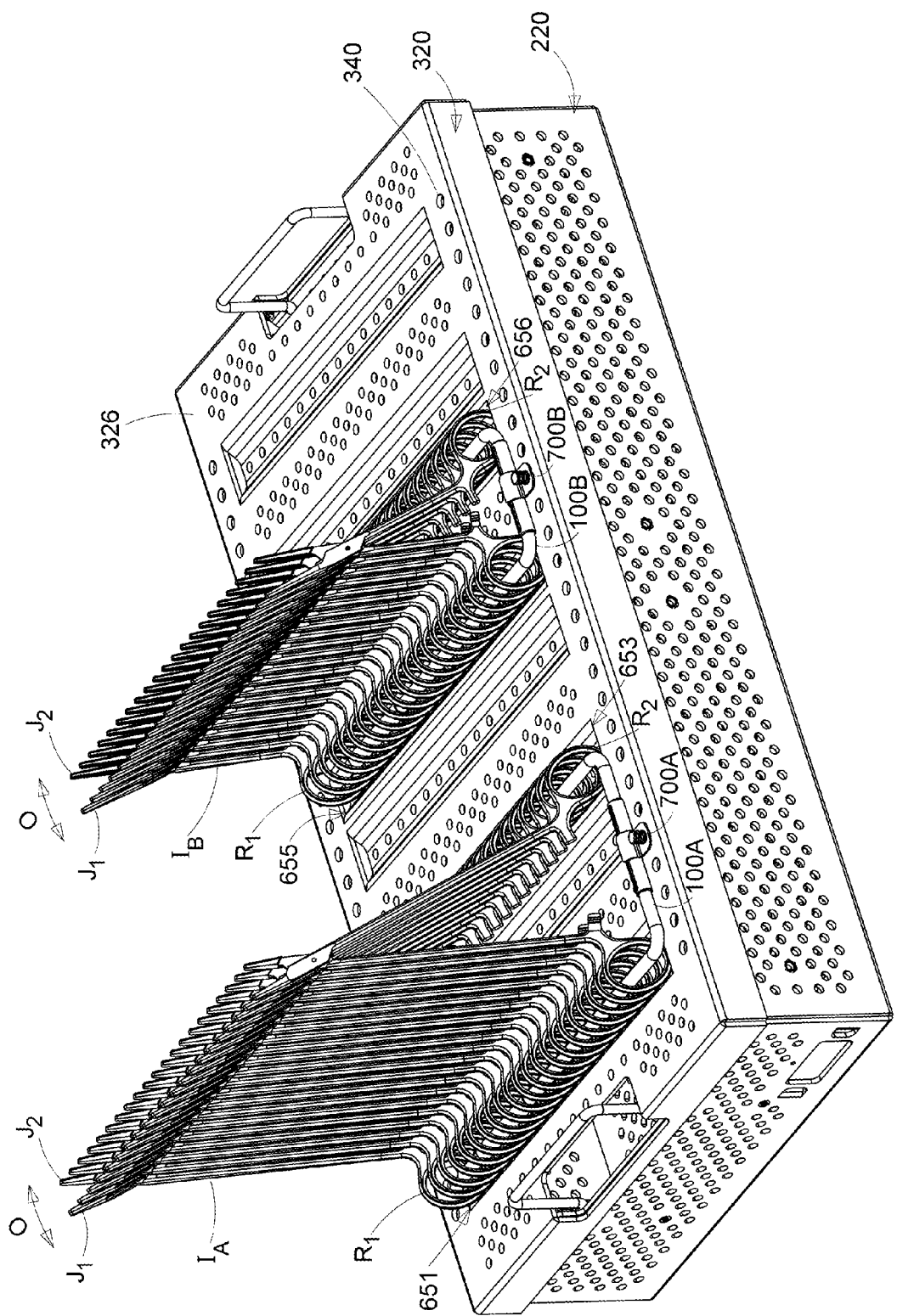
Fig. 6.2

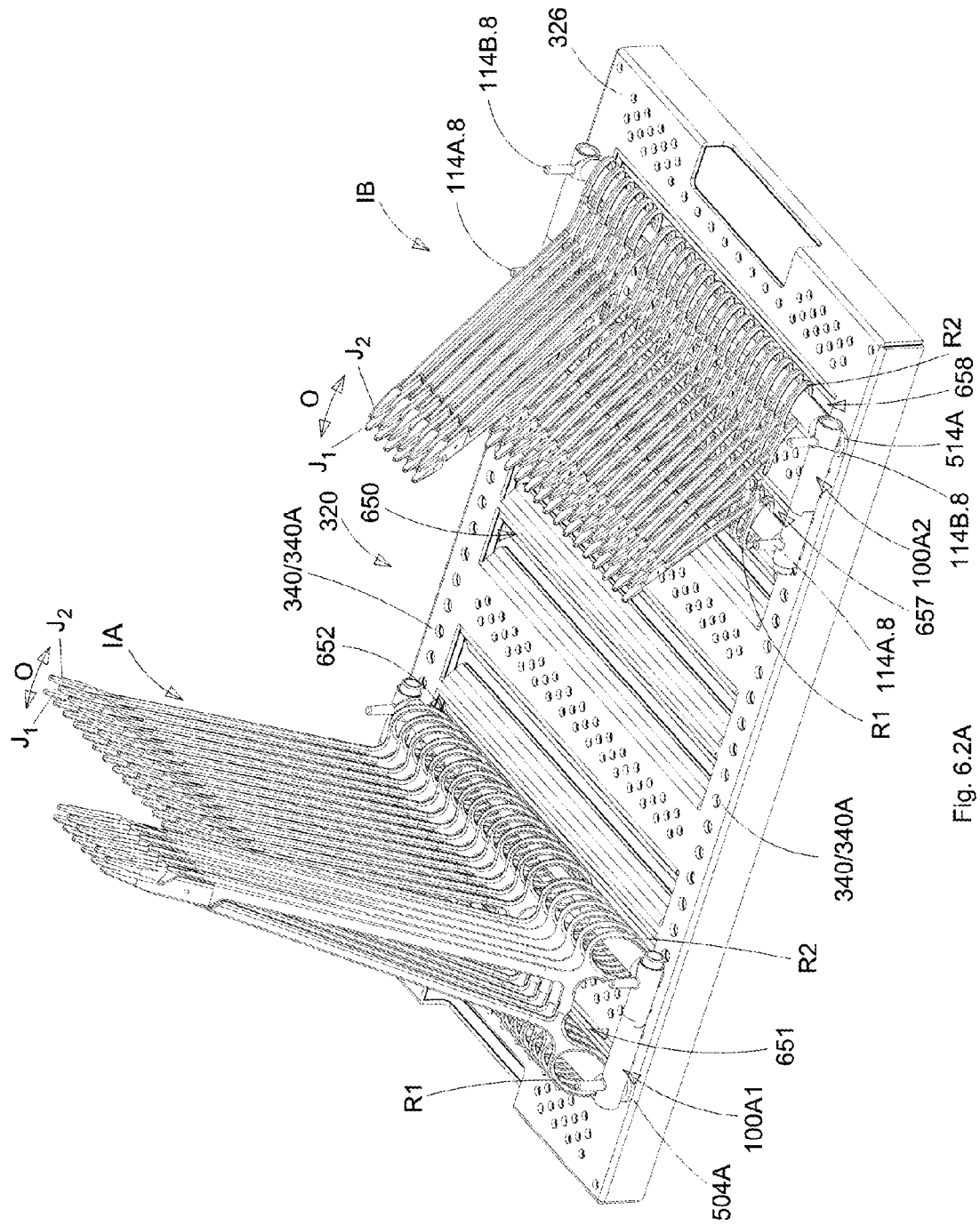
Fig. 6.2A

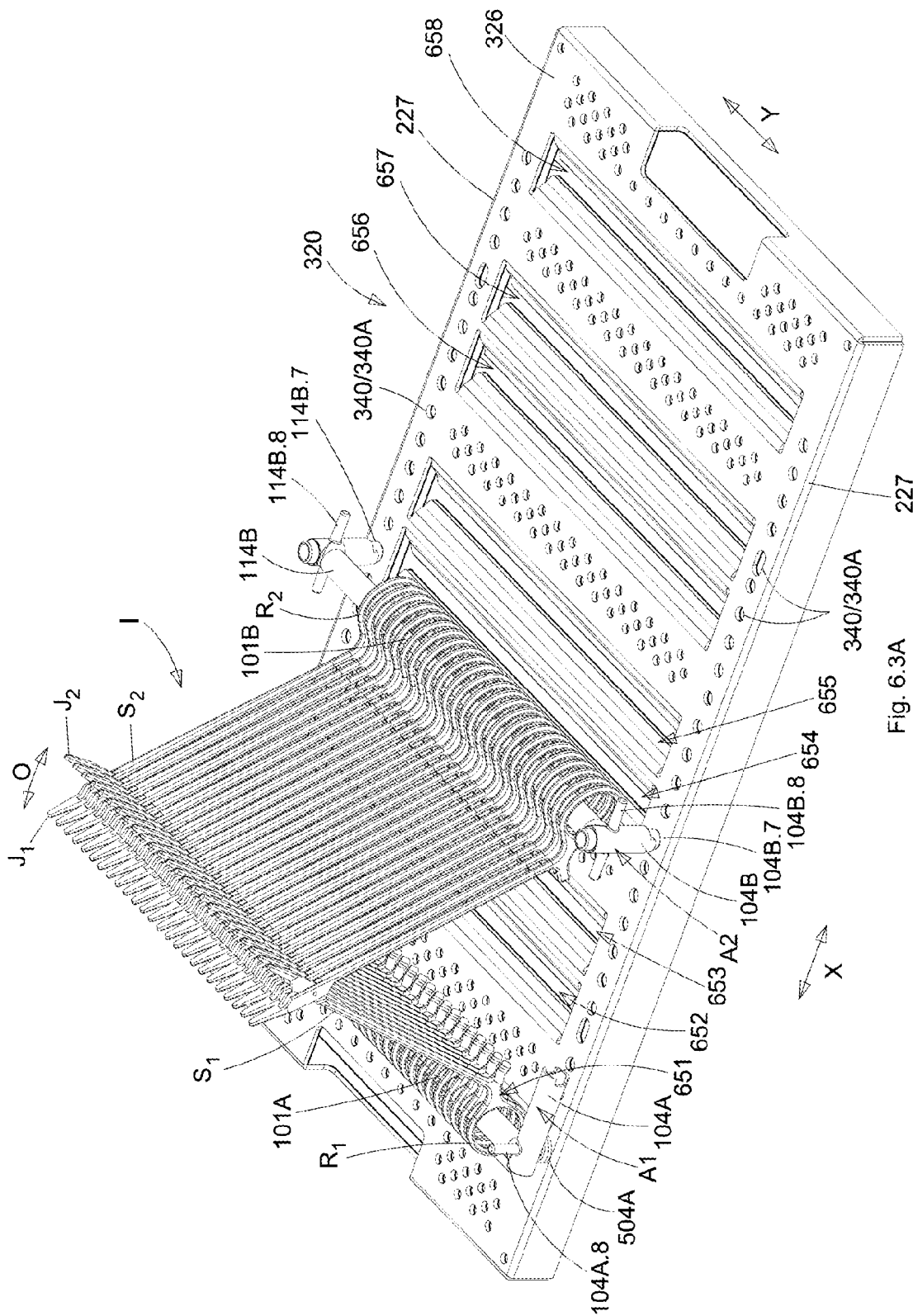
Fig. 6.3A

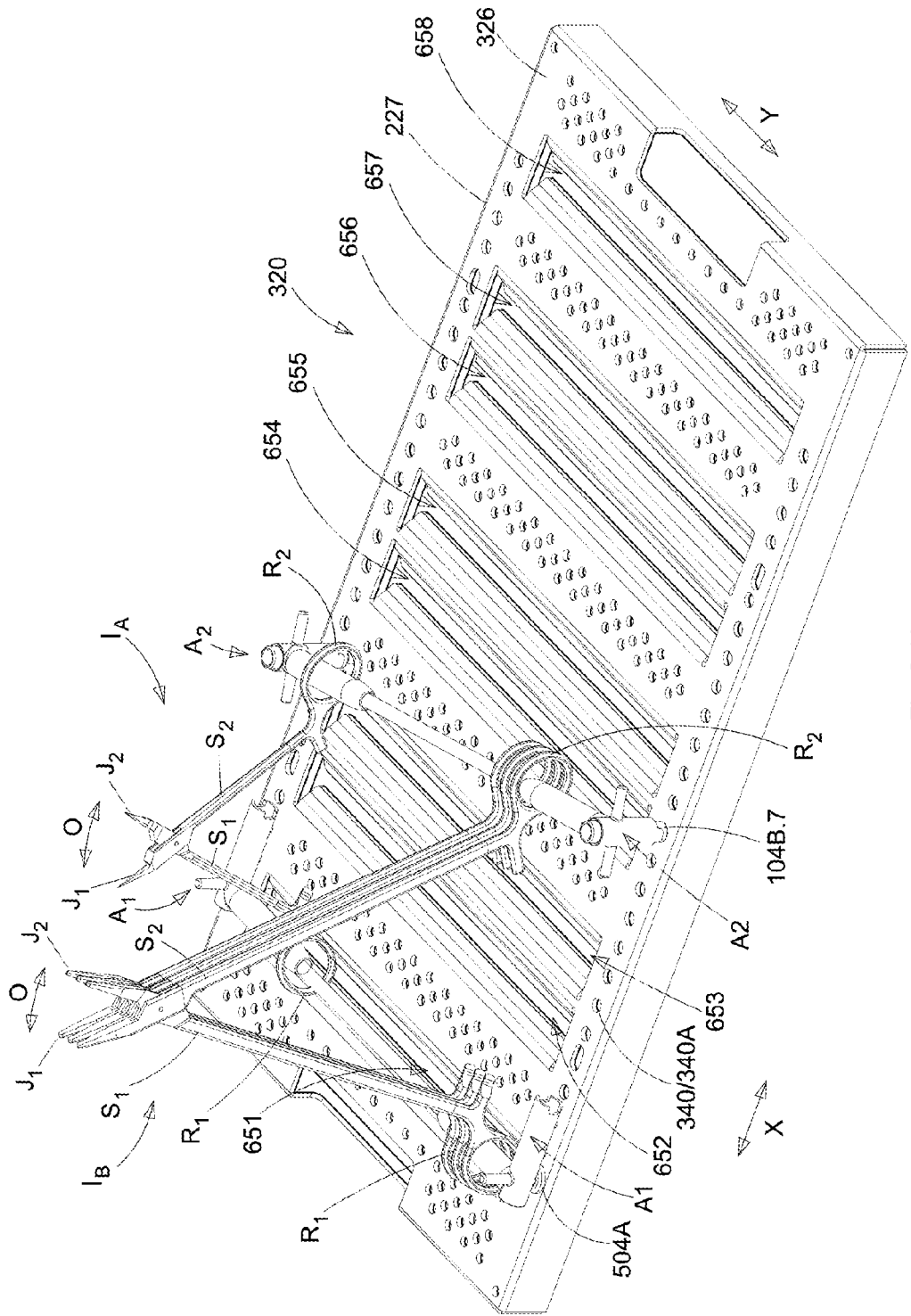
Fig. 6.4A

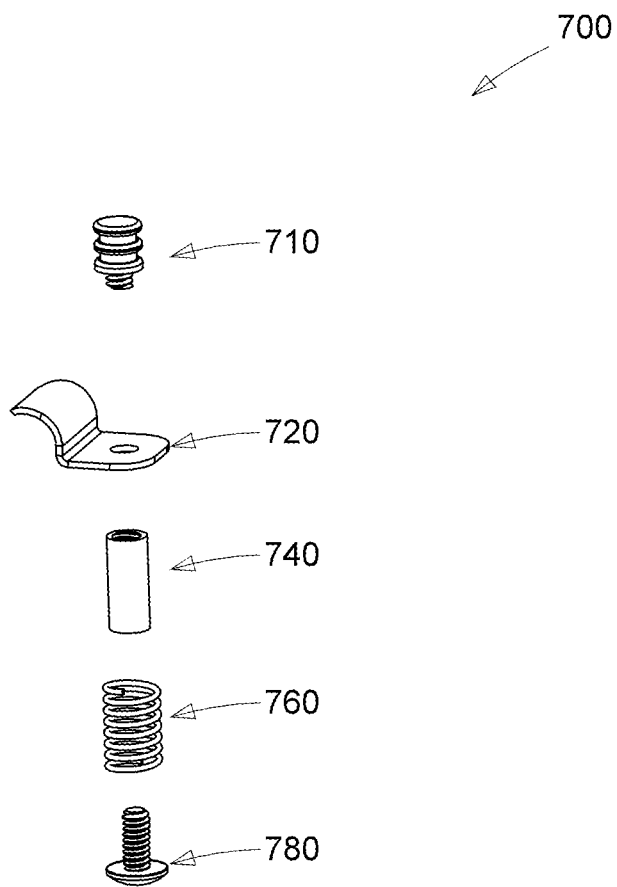
Fig. 7.1

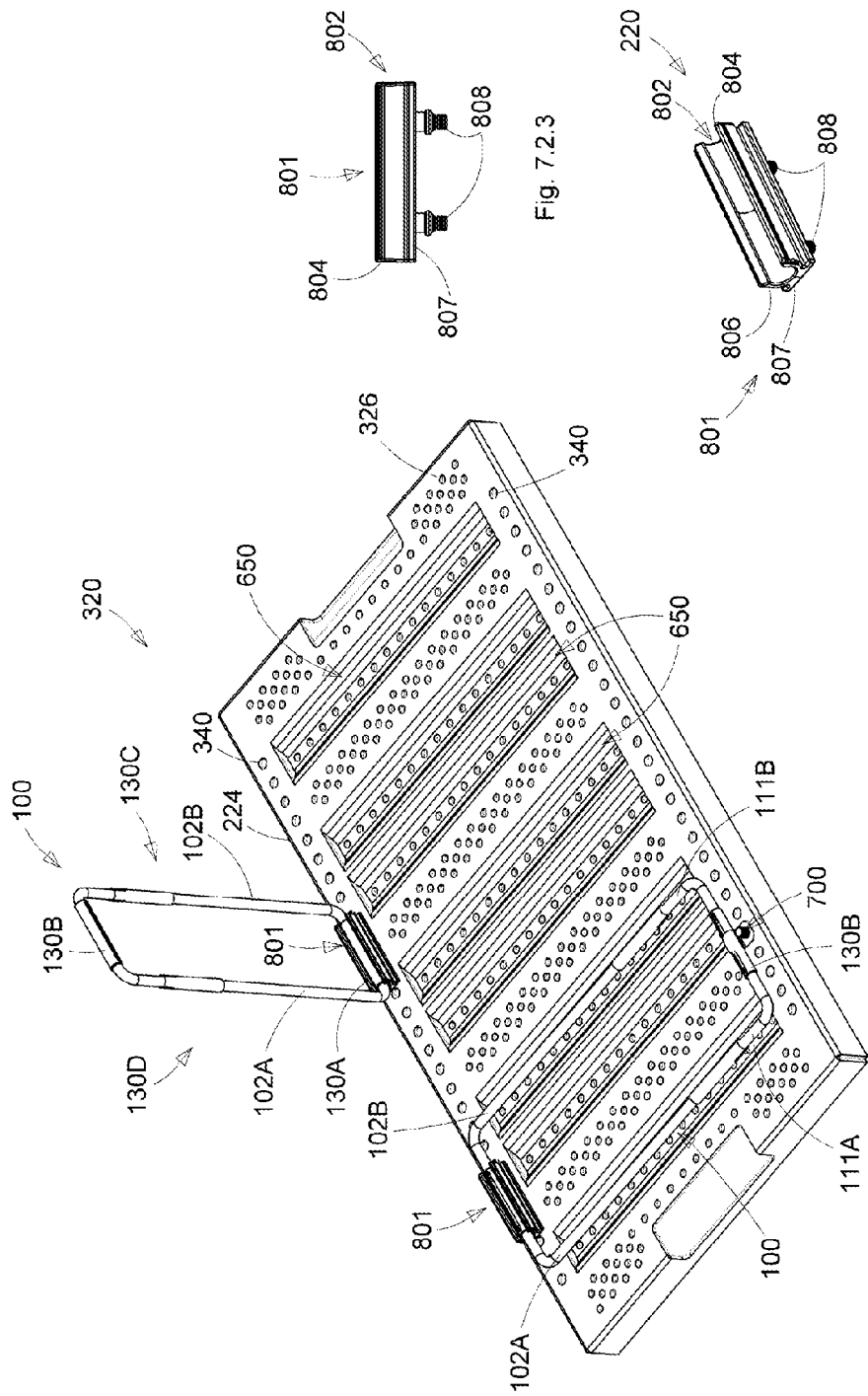

ADJUSTABLE SURGICAL INSTRUMENT STRINGER WITH PEGS, TRAY SYSTEM, AND METHOD OF STERILIZATION

PRIORITY CLAIM

To the full extent permitted by law, the present United States Non-provisional Patent Application, is a Divisional Application and hereby claims priority to and the full benefit of United States Non-provisional Continuation-in-Part application entitled "Adjustable Surgical Instrument Stringer with Pegs, Tray System, and Method of Sterilization", having assigned Ser. No. 13/761,986, filed on Feb. 7, 2013; which is a Continuation-in-Part of United States Non-provisional application entitled "Adjustable Surgical Instrument Stringer, Tray System, and Method of Sterilization," having assigned Ser. No. 13/570,236, filed on Aug. 8, 2012 (a continuation-in-part of application Ser. No. 13/284,099, filed on Oct. 28, 2011) and United States Non-provisional application entitled "Surgical Instrument Tray System and Method of Sterilization," having assigned Ser. No. 13/284,099, filed on Oct. 28, 2011, incorporated herein by reference in its entirety.

TECHNICAL FIELD

The disclosure generally relates to surgical instrument receptacle, organizational system and, more specifically, is related to a stringer and tray system for retaining a collection of surgical instruments for sterilization, transport and storage.

BACKGROUND

Present day surgical procedures regularly use sets of pre-selected surgical instruments for a specified surgical procedure, such as clamps, hemostat, forceps, scissors, retractors, and the like. These instruments are regularly grouped together to form a set. The set of surgical instruments is stored in a sterilized condition until required for surgery. Prior to sterilization the set of surgical instruments is subject to a time consuming multi-step sorting, identifying, grouping, cleaning and sterilization process. The set of surgical instruments is collected post operation, co-mingled in a wire mesh basket or holed tray for transport to the central sterile processing area. Next, the basket or tray of surgical instruments is placed in a wash sink to brush and manually wash the surgical instruments to remove any foreign debris, such as tissue or dried body fluid. Next, the basket or tray of surgical instruments is transported to and run through an automated washer/decontaminator. Next, the basket or tray of surgical instruments is transported to and emptied out on a sorting table where a technician inspects, counts and sorts each surgical instrument into groupings of instruments for a specified surgical procedure. Next, pivoting or hinged scissor-like surgical instruments are commonly sequentially grouped using a fixed stringer, bar or retaining rod positioned through both of the finger rings or ring handles, and the set is laid or positioned in a basket or tray. Next, the basket or tray of surgical instruments is placed in a sealed container and sealed before entering the sterilization machine. Next, the wrapped or containerized basket or tray of surgical instruments is placed in an industrial sterilization machine/autoclave for sterilization of the surgical instruments. Next, the sealed sterilization container of surgical instruments is stored until transported to an operating area for use as required. When needed the sterilized surgical instruments are transported to the operating room where the surgical instruments are removed from the basket or tray and arranged on a stand or instrument roll in a configuration that enables efficient transfer to a surgeon.

Much time is utilized during the process of cleaning, sorting, counting, and grouping procedure for the assembly and sterilization of surgical instruments. In addition, the onset of infectious diseases has dramatically increased the biohazard risk for medical personnel and central sterile personnel handling post operation cleaning, sorting, counting, and grouping of surgical instruments due to potential contact with sharp surgical instruments, such as needles. Such contact may result in loss of work for recovery, testing for contamination, and/or a workers compensation claim.

Furthermore, surgical instruments are often damaged when transported, stacked one on the other as well as when the surgical instruments are emptied out on a sorting table for a technician to inspect, count, and sort. Such handling may scratch, bend and may even break the surgical instruments resulting in increased cost to replace such instruments, which are often delicate and expensive. Such damage to the surgical instruments reduces the life expectancy of the surgical instruments resulting in increased medical costs to replace the surgical instruments. Moreover, if such damaged surgical instruments are accidentally returned to the operating room, such surgical procedures may be delayed or cancelled due to non-functioning surgical instruments causing lost revenue for the surgery center and an upset surgical team and patients in queue.

Still further, the environmental impact of the above multi-step process of pre-washing, automated washer/decontaminator, and running the surgical instruments through industrial sterilization machine/autoclave requires large quantities of water, sterilization chemicals and energy.

Yet still further, counting the surgical instruments before and after surgical procedures is particularly important for ensuring that no instruments are left in the patient after the operation procedure has been completed.

Yet still further, one problem with fixed or hinged stringers, bars or retaining rods is that the stringer is not adjustable to string, group or accommodate a variety of surgical instruments nor do such fixed stringers enable adjustment to hold or maintain a variety of surgical instruments in an open position ready for sorting, identifying, grouping, cleaning and sterilization.

Therefore, it is readily apparent that there is a recognizable unmet need for an adjustable surgical instrument stringer with pegs and tray system and method of sterilization that reduces the time spent cleaning, sorting, counting, identifying and grouping surgical instrument, extends the life expectancy of the surgical instruments, provides an adjustable stringer, and decreases the contamination potential of the surgical instruments by maintaining the surgical instruments in a side-by-side open configuration during cleaning and sterilization.

SUMMARY

Briefly described, in an example embodiment, the present apparatus and method overcomes the above-mentioned disadvantages and meets the recognized need for an adjustable surgical instrument stringer with pegs, tray system, and method of sterilization comprising, in general, a surgical instrument support tray configured to support a plurality of ring handled surgical instruments including, in general, a surface configured to support the plurality of surgical instruments, the surface further includes a plurality of holes formed therein, a stringer having two or more rod sections, wherein each the rod section is configured to be inserted in one ring handle of the plurality of ring handled surgical instruments, two or more angle sections, each angle section configured having one or more slidable connector sections, each slidable connector section configured to extend and retract along at least one of the two or more rod sections, and two or more releasable connectors, each releasable connector positioned between two of the two or more angle sections.

Moreover, a surgical instrument stringer, tray system, and method of sterilization having one or more axis adjustable stringer to be inserted into the finger rings or ring handles of the surgical instruments to sequentially group the surgical instruments, a surgical instrument tray and lid configured with a pattern of sterilization apertures, the lid having two or more recessed valleys configured to receive the stringer of ringed surgical instruments and releasably hold the surgical instrument therein and, thus such apparatus, functions to removeably secure the surgical instrument in a group for identification, cleaning, sterilization, and storage prior to surgery.

According to its major aspects and broadly stated, the present system meets the recognized need for an adjustable stringer configured to string the ring handles of one or more surgical instruments including two or more rod sections, each rod section configured with at least one angle section therein, and wherein each rod section is configured to be inserted in one ring handle of the one or more surgical instruments, and two or more slidable coupler sections, each slidable coupler section configured to extend and retract two of said two or more rod sections.

In a further exemplary embodiment of adjustable stringer configured to string the ring handles of one or more surgical instruments, the stringer including two or more rod sections, wherein each rod section is configured to be inserted in one ring handle of the one or more surgical instruments, two or more angle sections, each angle section configured having one or more slidable connector sections, each slidable connector section configured to extend and retract along at least one of the two or more rod sections, and two or more releasable connectors, each releasable connector positioned between two of the two or more angle sections.

In a further exemplary embodiment of a surgical instrument support tray configured to surgical instrument support tray configured to support a plurality of ring handled surgical instruments including, in general, a surface configured to support the plurality of surgical instruments, the surface further includes a plurality of holes formed therein, a stringer having two or more rod sections, wherein each rod section is configured to be inserted in one ring handle of the plurality of ring handled surgical instruments, two or more angle sections, each angle section configured having one or more slidable connector sections, each slidable connector section configured to extend and retract along at least one of the two or more rod sections, and two or more releasable connectors, each releasable connector positioned between two of the two or more angle sections.

In a further exemplary embodiment of a surgical instrument support tray configured to support a plurality of ring handled surgical instruments including a surface configured to support the plurality of surgical instruments, the surface further includes two or more valleys formed in parallel in the surface and configured to receive the ring handled surgical instruments, and a stringer having at least two rod sections, each rod section configured to be inserted in one ring handle of the plurality of ring handled surgical instruments.

In a further exemplary embodiment of a method of organizing surgical instruments having ring handles including the steps of providing a stringer having two or more rod sections, wherein each rod section is configured to be inserted in one ring handle of the one or more surgical instruments, two or more angle sections, each angle section configured having one or more slidable connector sections, each slidable connector section configured to extend and retract along at least one of the two or more rod sections, each angle section further configured having at least one peg, and two or more releasable connectors, each releasable connector positioned between two of the two or more angle sections, inserting each rod section in one ring handle of the one or more surgical instruments to group the one or more surgical instruments, providing a surface configured to support the plurality of surgical instruments, the surface further comprises a plurality of holes configured to enable sterilant to flow therethrough, adjusting the two or more slidable coupler sections of the stringer to fit the plurality of holes, and positioning the at least one peg of each angle section of the stringer in one of the plurality of holes to releasably retain the ring handles of the surgical instruments evenly spaced in an open jaw position.

In a further exemplary embodiment of a method of organizing surgical instruments having ring handles comprising the steps of providing a stringer having two or more rod sections, each rod section configured with at least one angle section therein and two or more slidable coupler sections, each slidable coupler section configured to extend and retract two of the two or more rod sections, inserting each rod section in one ring handle of the one or more surgical instruments to group the one or more surgical instruments, providing a surface configured to support the plurality of surgical instruments, the surface further comprises two or more valleys formed in parallel in the surface and configured to receive the ring handled surgical instruments, adjusting the two or more slidable coupler sections of the stringer to fit the two or more valleys formed in parallel in the surface, and positioning the stringer of the ring handled surgical instruments in two of the two or more valleys formed in parallel in the surface to releasably retain the ring handles of the surgical instruments evenly spaced in an open jaw position.

Accordingly, a feature of the adjustable surgical instrument stringer, tray system, and method of sterilization is its ability to reduce the time required to identify, clean, sort, count, and group surgical instrument between surgeries.

Another feature of the adjustable surgical instrument stringer, tray system, and method of sterilization is its ability to organize, protect and enable thorough cleaning and sterilization of surgical instruments.

Still another feature of the adjustable surgical instrument stringer, tray system, and method of sterilization is its ability to accommodate a variety of surgical instruments, such as size, shape, angle of bend, tip type, instruments purpose and the like all in one support tray system.

Yet another feature of the adjustable surgical instrument stringer, tray system, and method of sterilization is its ability to rapidly identify the appropriate instrument in the tray during sorting, counting, and grouping of the surgical instrument post-surgery, during pre-wash, pressure washing, sorting, grouping, sterilization or storage for pre-surgical use.

Yet another feature of the adjustable surgical instrument stringer, tray system, and method of sterilization is its ability to rapidly identify and select the appropriate surgical instrument during surgery without confusion and lapse of time and to also identify all surgical instruments post-surgery.

Yet another feature of the adjustable surgical instrument stringer, tray system, and method of sterilization is its ability to reduce inefficiency and waste in turning around sterile surgical instruments as set forth in the Affordable Care Act.

Yet another feature of the adjustable surgical instrument stringer, tray system, and method of sterilization is its ability to decrease the loss of surgical instruments, decrease the time to count the surgical instruments before and after surgical procedures, and decrease assembly time of surgical instrument sets.

Yet another feature of the adjustable surgical instrument stringer, tray system, and method of sterilization is its ability to reduce surgical instrument inventory or reduce the need for additional capital expenditures due to increased surgical volume as a result of more efficient processing time.

Yet another feature of the adjustable surgical instrument stringer, tray system, and method of sterilization an adjustable surgical instrument stringer, tray system, and method of sterilization is its ability to enable a uniform cleaning process for reducing the potential for surgical site infection.

Yet another feature of the adjustable surgical instrument stringer, tray system, and method of sterilization is its ability to reduce the occurrences of malfunctions, delays or cancellations during the surgical procedure due to improperly inspected or cleaned surgical instruments.

Yet another feature of the adjustable surgical instrument stringer, tray system, and method of sterilization is its ability to reduce the capital budget for repairs associated with care and handling of surgical instruments.

Yet another feature of the adjustable surgical instrument stringer, tray system, and method of sterilization is its ability to integrate the surgical instrument support tray as the tray top of box like container.

Yet another feature of the adjustable surgical instrument stringer, tray system, and method of sterilization is its ability to reduce the number of sharps being sent to central sterile and the reduction of accidents associated with needle/sharps injuries.

Yet another feature of the adjustable surgical instrument stringer, tray system, and method of sterilization is its ability to inventory surgical blades and needles after being disengaged therefrom.

Yet another feature of the adjustable surgical instrument stringer, tray system, and method of sterilization is its ability to color coordinate a group of trays within a surgical service for easy identification for specific surgical specialties.

Yet another feature of the adjustable surgical instrument stringer, tray system, and method of sterilization is its ability to reduce surgical instrument damage when transporting, stacking, sorting, inspecting, counting, and/or when emptying out on a sorting table for a technician to inspect, count, and sort. Such handling may scratch, bend and may even break the surgical instruments resulting in increased cost to replace such instruments, which are often delicate and expensive. Such damage to the surgical instruments reduces the life expectancy of the surgical instruments resulting in increased medical costs to replace the surgical instruments.

Yet another feature of the adjustable surgical instrument stringer, tray system, and method of sterilization is its ability to sort, identify, group, clean, and sterilize and to further prevent damaged or improperly cleaned surgical instruments from accidentally being returned to the operating room, where such surgical procedures may be delayed or cancelled due to non-functioning surgical instruments and further causing lost revenue for the surgery center.

Yet another feature of the adjustable surgical instrument stringer, tray system, and method of sterilization is its ability to reduce the environmental impact of the multi-step process of pre-washing, automated washer/decontaminator, and running the surgical instruments through industrial sterilization machine/autoclave to reduce the requirements for large quantities of water, sterilization chemicals and energy.

Yet another feature of the adjustable surgical instrument stringer, tray system, and method of sterilization is its ability to provide an adjustable stringer to group or accommodate a variety of surgical instruments and provide adjustment to hold or maintain a variety of surgical instruments in an open position ready for sorting, identifying, grouping, cleaning and sterilization.

Yet another feature of the adjustable surgical instrument stringer with pegs, tray system, and method of sterilization is its ability to provide one or more pegs to be utilized to affix stringer and/or a group of surgical instrument bound together by stringer to the tray or tray top.

Yet another feature of the adjustable surgical instrument stringer with pegs, tray system, and method of sterilization is its ability to provide a linear adjustment or latch and release connector between sections.

Yet another feature of the adjustable surgical instrument stringer with pegs, tray system, and method of sterilization is its ability to provide a stringer that may be positioned in or across valleys on tray top by adjusting the stringer wherein the surgical instruments may be retained in parallel or non-parallel to the valleys, evenly spaced and an open jaw position by surgical instrument support tray system.

Yet another feature of the adjustable surgical instrument stringer with pegs, tray system, and method of sterilization is its ability to provide a stringer that accommodates shorter shanked surgical instrument sets and longer shanked surgical instrument sets, on one stringer in a wide open position for better cleaning and sterilization purposes and to enable easy identification, pressure washing, sorting, counting, and grouping of surgical instruments.

These and other features of the adjustable surgical instrument stringer with pegs, tray system, and method of sterilization will become more apparent to one skilled in the art from the following Brief Description of the Drawings, Detailed Drawings, Detailed Description and Claims when read in light of the accompanying drawings.

BRIEF DESCRIPTION OF THE DRAWINGS

The present adjustable surgical instrument stringer with pegs, tray system, and method of sterilization will be better understood by reading the Detailed Description of the embodiments with reference to the accompanying drawings, in which like reference to numerals denote similar structures and refer to like elements throughout, and in which:

FIG. 2 is a top view, side view and bottom view of the stringer of FIG. 1;

FIG. 2.1 is a top view of the stringer of FIG. 1;

FIG. 2.2 is a side view of the stringer of FIG. 1;

FIG. 2.3 is an end view of the stringer of FIG. 1;

FIG. 4.1 is top view of an example surgical instrument for storage in the surgical instrument support tray system shown herein;

FIG. 4.2 is perspective view of a plurality of surgical instruments of FIG. 4.1 shown strung together with stringer of FIG. 1;

FIG. 5.1 is perspective view of an example embodiment box like tray bottom and lid surgical instrument support tray system with exemplary adjustable stringer position thereon;

FIG. 5.2 is an exploded perspective view of an example embodiment box like tray bottom and lid surgical instrument support tray system with exemplary adjustable stringer;

FIG. 5.2.1 is a perspective view of an example embodiment box like tray bottom;

FIG. 5.2.2 is a perspective view of an example embodiment box lid surgical instrument support with exemplary adjustable stringer;

FIG. 5.3 is a top and cross sectional view of an example embodiment box lid and surgical instrument support system;

FIG. 5.3.1 is a top view of an example embodiment box lid and surgical instrument support system;

FIG. 5.3.2 is a cross sectional view of an example embodiment box lid and surgical instrument support system;

FIG. 5.3.3 is a cross sectional view of an example embodiment box lid and surgical instrument support system;

FIG. 5.4 is a top and cross sectional view of an example embodiment box like tray bottom and internal small box support system;

FIG. 5.4.1 is a cross sectional side view of an example embodiment box like tray bottom and internal small box support system;

FIG. 5.4.2 is a top view of an example embodiment box like tray bottom and internal small box support system;

FIG. 5.5 is perspective view of an example embodiment box like lid or top for a surgical instrument support tray system with exemplary stringer of FIG. 1 positioned thereabove;

FIG. 6.1 is a perspective view of an example embodiment of a surgical instrument support tray system with exemplary adjustable stringers shown in two positions affixed to the top or lid of the surgical instrument support tray system;

FIG. 6.1A is a perspective view of an example embodiment of a box like lid or top of a surgical instrument support tray system with exemplary stringers of FIG. 1 shown in two positions releasably affixed to the top or lid of the surgical instrument support tray system;

FIG. 6.2 is a perspective view of an example embodiment of a surgical instrument support tray system with a plurality of surgical instrument sets held by exemplary adjustable stringers to the top of the surgical instrument support tray system;

FIG. 6.2A is a perspective view of an example embodiment of a lid or top for a surgical instrument support tray system with a plurality of surgical instrument sets held by exemplary stringers of FIG. 1 to the top of the surgical instrument support tray system;

FIG. 6.3A is a perspective view of an example embodiment of a lid or top for a surgical instrument support tray system with a plurality of surgical instrument sets held by exemplary unlatched stringer of FIG. 1 to the top of the surgical instrument support tray system with ring handles positioned parallel to valleys formed in the lid or top;

FIG. 6.4A is a perspective view of an example embodiment of a lid or top for a surgical instrument support tray system with a plurality of surgical instrument sets held by exemplary unlatched stringer of FIG. 1 to the top of the surgical instrument support tray system with ring handles positioned non-parallel to valleys formed in the lid or top;

FIG. 7.1 is an exploded perspective view of the attachment device of FIG. 5.2.2;

FIG. 7.2 is a perspective view of an alternate exemplary attachment device of FIG. 7.1;

FIG. 7.2.1 is a perspective view of an alternate exemplary attachment device of FIG. 7.1;

FIG. 7.2.2 is a perspective view of an alternate exemplary attachment device of FIG. 7.2.1;

FIG. 7.2.3 is a side view of an alternate exemplary attachment device of FIG. 7.2.1.

It is to be noted that the drawings presented are intended solely for the purpose of illustration and that they are, therefore, neither desired nor intended to limit the disclosure to any or all of the exact details of construction shown, except insofar as they may be deemed essential to the claimed invention.

DETAILED DESCRIPTION

In describing the exemplary embodiments of the present disclosure as illustrated in FIGS. 1-8 specific terminology is employed for the sake of clarity. The present disclosure, however, is not intended to be limited to the specific terminology so selected, and it is to be understood that each specific element includes all technical equivalents that operate in a similar manner to accomplish similar functions. Embodiments of the claims may, however, be embodied in many different forms and should not be construed to be limited to the embodiments set forth herein. The examples set forth herein are non-limiting examples, and are merely examples among other possible examples.

Figure 1:
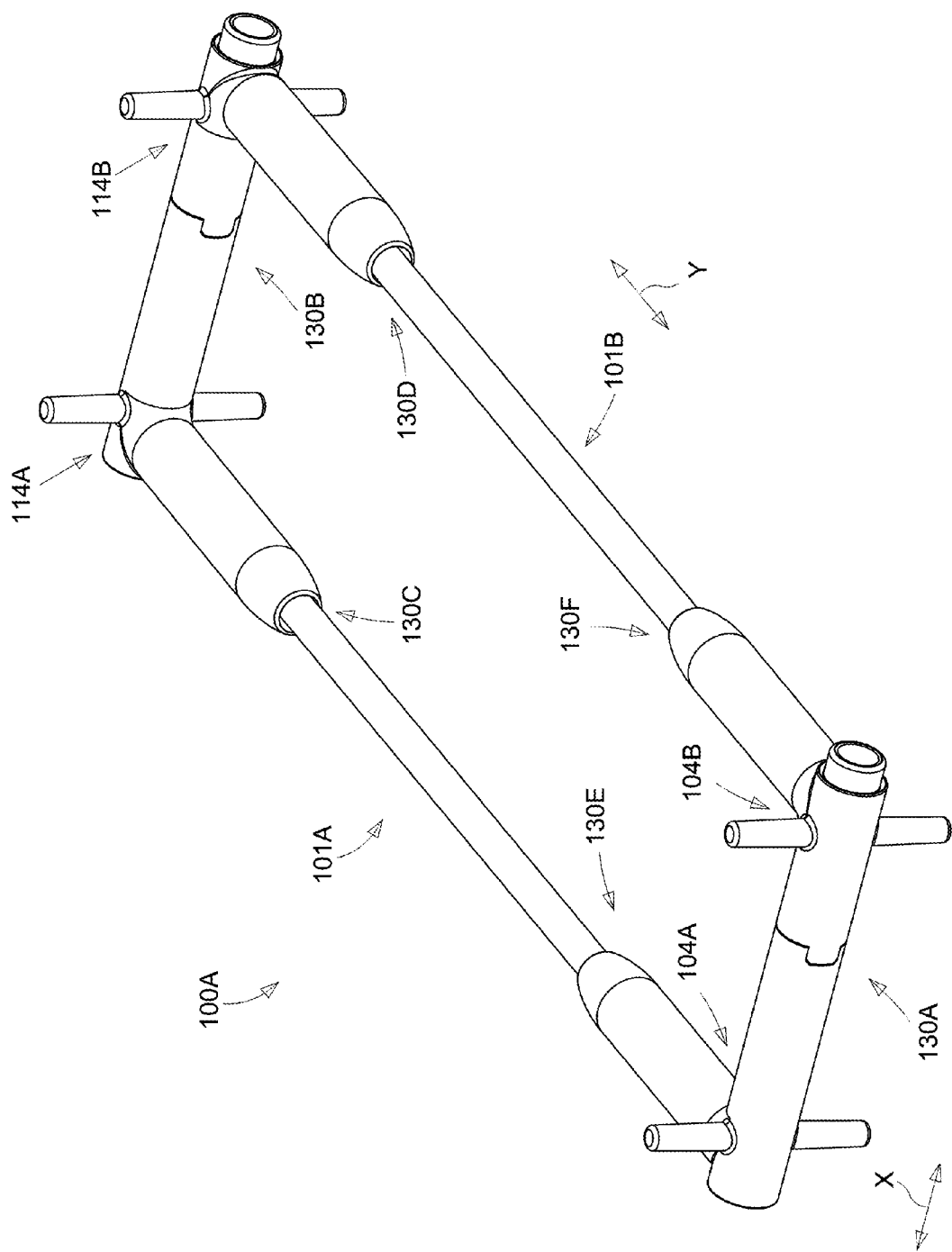
FIG. 1 is a perspective view of an example stringer.

Referring now to FIG. 1 there is illustrated a perspective view of an exemplary adjustable or fixed bar or retaining rod, such as stringer 100A. Preferably, stringer 100A includes one or more bars, tubes, conduits or the like, such as rod 101A/B, one or more bends, corners, angles, right angle, acute angle, curves, or turns, such as angle sections 104A/B or 114A/B, and one or more expand and contract sections, slidable sections, latchable sections, telescope, or releasable sections, such as connector 130A/B/C/D/E/F. It is contemplated herein that other configurations of connector 130A/B/C/D/E/F known to one of ordinary skill in the art, such as other connector configurations, multi segment connector, telescopic slidable connector sections or the like to accommodate larger surgical instruments I are included herein. It is further contemplated herein that rod 101A/B and angle sections 104A/B or 114A/B may be formed as a plurality of pieces or parts for assembly as a whole stringer 100A or as one or more single elements for assembly as a whole stringer 100A. Stringer 100A is preferably configured as an adjustable rectangular configuration with adjustments in one or more axis, such as x axis X and/or y axis Y via connector 130A/B/C/D/E/F; however, other configurations, such as square, trapezoid, trapezium, or the like and other adjustments or adjustment mechanisms in and between axis are contemplated herein.

Referring now to FIG. 2 there is illustrated a top view, side view and bottom view of stringer 100A. FIG. 2.1 further illustrates the rectangular configuration of rods 101A/B and 111A/B, angle sections 104A/B and 114A/B, and connector 130A/B/C/D/E/F. FIG. 2.2 further illustrates the linear adjustment capability in the y axis Y between rod 101A and angle sections 104A and/or 114A via connector section 130C/F configured to enable releasable extension and retraction of rod 101A in and out therein of connector 130C/F. It is contemplated herein that rod 101B may be configured to enable releasable extension and retraction of rod 101B in and out therein of connector section 130D/E. FIG. 2.3 further illustrates the linear adjustment or latch and release capability in the x axis X between angle sections 104A and 104B via connector 130A. It is contemplated herein that connector 130B likewise may be configured to enable the linear adjustment or latch and release capability in the x axis X between angle sections 114A and 114B via connector 130B.

Stringer 100A is preferably formed of a suitable surgical material, such as stainless steel, aluminum, metal, metal alloys, shape memory alloys, carbon fibers, nylon, ceramic or the like, capable of providing structure whether as a solid or hollow stringer 100A. Preferably, the material includes other suitable characteristics, such as durability, rigidity, stain-resistance, bacteria-resistant, light weight, chemical inertness, oxidation resistance, ease of workability, or other beneficial characteristic understood by one skilled in the art. Moreover, stringer 100A is preferably configured having a cross-sectional circular diameter; however, other configurations, such as square or the like, are contemplated herein. Stringer 100A is preferably solid for the purpose of preventing any interior surface capable of colonizing bacteria, viruses or other infectious diseases and difficult for sterilization chemicals to reach; however, a hollow interior is contemplated herein if such interior is sealed or alternatively if a plurality of holes or apertures are present to enable sterilization of the interior surface of stringer 100A.

Figure 3:
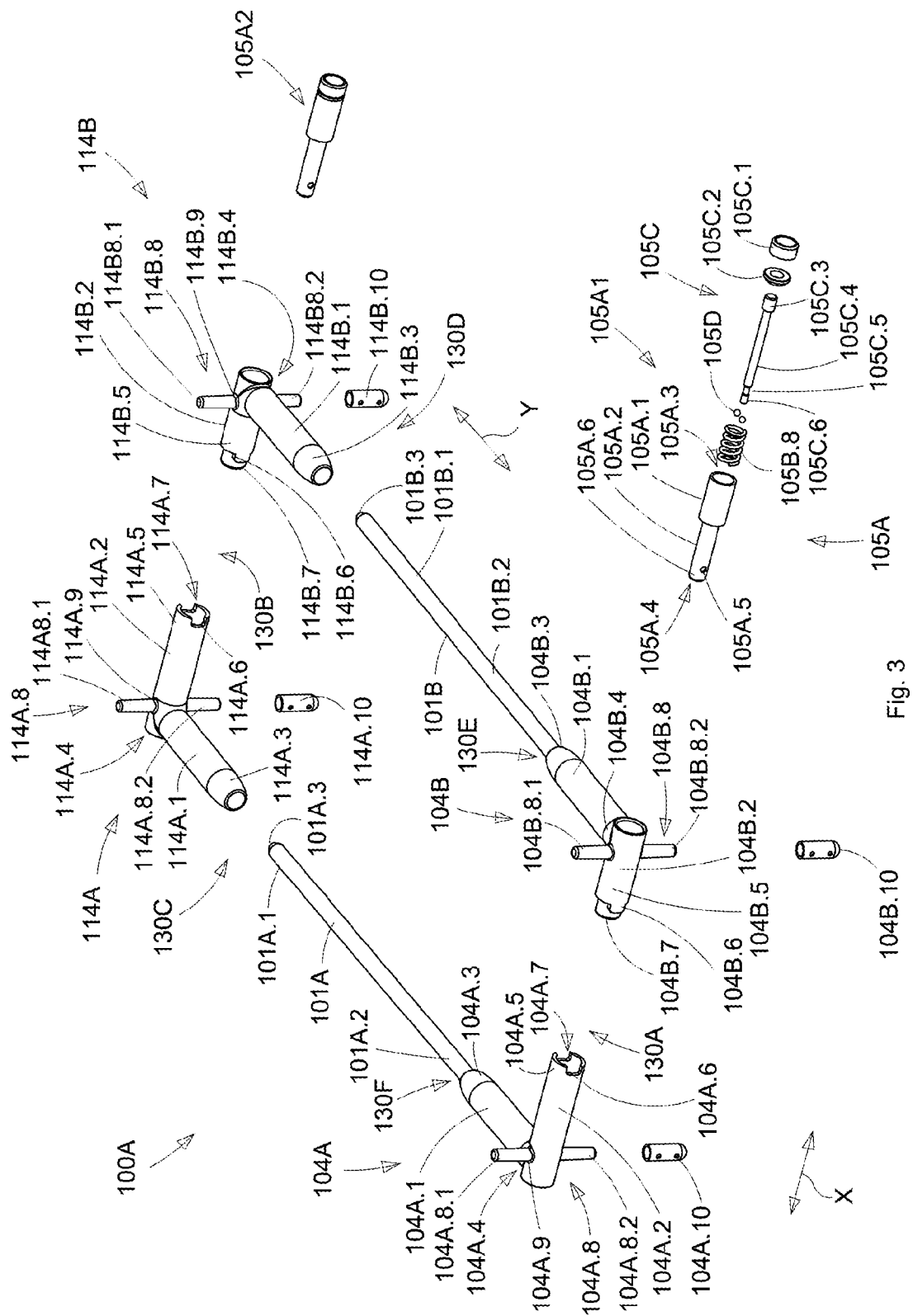
FIG. 3 is an exploded perspective view of the stringer of FIG. 1.

Referring now to FIG. 3 there is illustrated an exploded view of rod 101A, rod 101B, angle sections 104A/B or 114A/B, and connectors 130A/B/C/D/E/F of stringer 100A. Preferably rod 101A includes first rod end 101A.1 and second rod end 101A.2. First rod end 101A.1 preferably includes a solid end, rounded end, pointed end, or cover, such as rod end cap 101A.3. Second rod end 101A.2 preferably transitions to or is releasably connected to angle section 104A. Preferably rod 101B includes first rod end 101B.1 and second rod end 101B.2. First rod end 101B.1 preferably includes a solid end, rounded end, pointed end, or cover, such as rod end cap 101B.3. Second rod end 101B.2 preferably transitions to or is releasably connected to angle section 104B.

Preferably angle section 104A includes first connector section 104A.1 configured approximately perpendicular, curved, or right angled to second connector section 104A.2 and both are preferably adjoined to one another at a common intersection 104A.4. First connector section 104A.1 preferably includes a transition end or tapered end, such as first connector end 104A.3 configured to releasably connect second rod end 101A.2 of rod 101A thereto first connector section 104A.1 of angle section 104A. It is recognized herein that connector 130F may be an adhesive, compression fitting, mechanical fitting, weld, single molded component of rod 101A and angle section 104A or the like. It is alternatively contemplated herein that connector 130F may preferably comprise a fixed connection therebetween first connector end 104A.3 of first connector section 104A.1 and second rod end 101A.2 of rod 101A. Moreover, second connector section 104A.2 of angle section 104A preferably includes a transition end or fitted end, such as second connector end 104A.5 configured to releasably connect second connector section 104A.2 of angle section 104A thereto angle section 104B. Preferably, second connector end 104A.5 includes receptacle 104A.7 and further includes first edge 104A.6 configured preferably to match, fit, (notched-slotted) and/or receive angle section 104B to aid in the proper alignment of angle sections 104A/B and to maintain rods 101A/B in alignment or parallel with each other. It is contemplated herein that receptacle 104A.7 and/or first edge 104A.6 may be alternatively configured to accommodate and/or releasably connect second connector section 104A.2 of angle section 104A thereto angle section 104B.

Preferably, second connector section 104A.2 of angle section 104A includes a pin, leg, support, or hanger, such as first peg 104A.8 configured approximately vertical, perpendicular or right angled to second connector section 104A.2 and extends above (first peg 104A.8.1) and/or below (first peg 104A.8.2) second connector section 104A.2. First peg 104A.8 is preferably inserted through conduit 104A.9 configured through second connector section 104A.2 or may have been formed as a part of second connector section 104A.2 or otherwise therein angle section 104A. It is contemplated herein that first peg 104A.8 may alternatively have likewise been positioned or formed as a part of first connector section 104A.1. Furthermore, first peg 104A.8 may be configured with grommet or cover 104A.10 to releasably affix or hold first peg 104A.8 thereto apertures 340 formed tray top 320.

It is contemplated herein that angle section 104A may be formed or molded as one piece including first connector section 104A.1, second connector section 104A.2, and first peg 104A.8.

Preferably angle section 104B includes first connector section 104B.1 configured approximately perpendicular, curved, or right angled to second connector section 104B.2 and both are preferably adjoined to one another at a common intersection 104B.4. First connector section 104B.1 preferably includes a transition end or tapered end, such as first connector end 104B.3 configured to releasably connect second rod end 101B.2 of rod 101B thereto first connector section 104B.1 of angle section 104B. It is recognized herein that connector 130E may be an adhesive, compression fitting, weld, mechanical connector, single molded component of rod 101B and angle section 104B or the like. It is alternatively contemplated herein that connector 130E may preferably comprise a fixed connection therebetween such as first connector end 104B.3 of first connector section 104B.1 and second rod end 101B.2 of rod 101B. Moreover, second connector section 104B.2 of angle section 104B preferably includes a transition end or fitted end, such as second connector end 104B.5 configured to releasably connect second connector section 104B.2 of angle section 104B thereto angle section 104A. Preferably, second connector end 104B.5 includes protrusion 104B.7 and further includes first edge 104B.6 configured preferably to match, fit, (notched-slotted) first edge 104A.6 and/or insert therein receptacle 104A.7 of angle section 104A to aid in the proper alignment of angle sections 104A/B and to maintain rods 101A/B in alignment or parallel with each other. It is contemplated herein that protrusion 104B.7 and/or first edge 104B.6 may be alternatively configured to accommodate and/or releasably connect second connector section 104B.2 of angle section 104B thereto angle section 104A.

Preferably, second connector section 104B.2 of angle section 104B includes a pin, leg, support, or hanger, such as second peg 104B.8 configured approximately vertical, perpendicular or right angled to second connector section 104B.2 and extends above (second peg 104B.8.1) and/or below (second peg 104B.8.2) second connector section 104B.2. Second peg 104B.8 is preferably inserted through conduit 104B.9 configured through second connector section 104B.2 or may have been formed as a part of second connector section 104B.2 or angle section 104B. It is contemplated herein that second peg 104B.8 may alternatively have been positioned or formed as a part of first connector section 104B.1. Furthermore, second peg 104B.8 may be configured with grommet or cover 104B.10 to releasably affix or hold second peg 104B.8 thereto apertures 340 formed tray top 320.

It is contemplated herein that angle section 104B may be formed or molded as one piece including first connector section 104B.1, second connector section 104B.2, and second peg 104B.8.

Preferably angle section 114A includes first connector section 114A.1 configured approximately perpendicular, curved, or right angled to second connector section 114A.2 and both are preferably adjoined to one another at a common intersection 114A.4. First connector section 114A.1 preferably includes a transition end or tapered end, such as first connector end 114A.3 configured to releasably and slidably connect first rod end 101A.1 of rod 101A thereto first connector section 114A.1 of angle section 114A. It is recognized herein that connector 130C may be an adhesive, compression fitting, weld, mechanical connector, single molded component of rod 101A and angle section 114A or the like. It is alternatively contemplated herein that connector 130C may preferably comprise a fixed connection therebetween first connector end 114A.3 of first connector section 114A.1 and first rod end 101A.1 of rod 101A. Moreover, second connector section 114A.2 of angle section 114A preferably includes a transition end or fitted end, such as second connector end 114A.5 configured to releasably connect second connector section 114A.2 of angle section 114A thereto angle section 114B. Preferably, second connector end 114A.5 includes receptacle 114A.7 and further includes first edge 114A.6 configured preferably to match, fit, (notched-slotted) and/or receive angle section 114B to aid in the proper alignment of angle sections 114A/B and to maintain rods 101A/B in alignment or parallel with each other. It is contemplated herein that receptacle 114A.7 and/or first edge 114A.6 may be alternatively configured to accommodate and/or releasably connect second connector section 114A.2 of angle section 114A thereto angle section 114B.

Preferably, second connector section 114A.2 of angle section 114A includes a pin, leg, support, or hanger, such as third peg 114A.8 configured approximately vertical, perpendicular or right angled to second connector section 114A.2 and extends above (third peg 114A.8.1) and/or below (third peg 114A.8.2) second connector section 114A.2. Third peg 114A.8 is preferably inserted through conduit 114A.9 configured through second connector section 114A.2 or may have been formed as a part of second connector section 114A.2 or angle section 114A. It is contemplated herein that third peg 114A.8 may alternatively have been positioned or formed as a part of first connector section 114A.1. Furthermore, third peg 114A.8 may be configured with grommet or cover 114A.10 to releasably affix or hold third peg 114A.8 thereto apertures 340 formed tray top 320.

It is contemplated herein that angle section 114A may be formed or molded as one piece including first connector section 114A.1, second connector section 114A.2, and third peg 114A.8.

Preferably angle section 114B includes first connector section 114B.1 configured approximately perpendicular, curved, or right angled to second connector section 114B.2 and both are preferably adjoined to one another at a common intersection 114B.4. First connector section 114B.1 preferably includes a transition end or tapered end, such as first connector end 114B.3 configured to releasably and slidably connect first rod end 101B.1 of rod 101B thereto first connector section 114B.1 of angle section 114B. It is recognized herein that connector 130D may be an adhesive, compression fitting, weld, mechanical connector, single molded component of rod 101B and angle section 114B or the like. It is alternatively contemplated herein that connector 130D may preferably comprise a fixed connection therebetween such as first connector end 114B.3 of first connector section 114B.1 and first rod end 101B.1 of rod 101B. Moreover, second connector section 114B.2 of angle section 114B preferably includes a transition end or fitted end, such as second connector end 114B.5 configured to releasably connect second connector section 114B.2 of angle section 114B thereto angle section 114A. Preferably, second connector end 114B.5 includes protrusion 114B.7 and further includes first edge 114B.6 configured preferably to match, fit, (notched-slotted) first edge 14A.6 and/or insert therein receptacle 114A.7 of angle section 104A to aid in the proper alignment of angle sections 114A/B and to maintain rods 101A/B in alignment or parallel with each other. It is contemplated herein that protrusion 114B.7 and/or first edge 114B.6 may be alternatively configured to accommodate and/or releasably connect second connector section 114B.2 of angle section 114B thereto angle section 114A.

Preferably, second connector section 114B.2 of angle section 114B includes a pin, leg, support, or hanger, such as fourth peg 114B.8 configured approximately vertical, perpendicular or right angled to second connector section 114B.2 and extends above (fourth peg 114B.8.1) and/or below (fourth peg 114B.8.2) second connector section 104B.2. Fourth peg 114B.8 is preferably inserted through conduit 114B.9 configured through second connector section 114B.2 or may have been formed as a part of second connector section 114B.2 or angle section 114B. It is contemplated herein that fourth peg 114B.8 may alternatively have been positioned or formed as a part of first connector section 114B.1. Furthermore, fourth peg 114A.8 may be configured with grommet or cover 114B.10 to releasably affix or hold fourth peg 114A.8 thereto apertures 340 formed tray top 320.

It is contemplated herein that angle section 114B may be formed or molded as one piece including first connector section 114B.1, second connector section 114B.2, and fourth peg 114B.8.

It is contemplated herein that pegs 104A.8, 104B.8, 114A.8, and 114B.8 may be removeable or slid in conduit 104A.9, 104B.9, 114A.9, and 114B.9, respectively, to enable stringer 100A to lie flat on a surface or to assist with stacking, sorting, inspecting, and counting of surgical instruments I, and additionally when positioning on a sorting table for a technician to inspect, count, and sort.

Stringer 100A further includes two or more connectors 130A/B/C/D/E/F for extension and retraction of rods 101A/B. Preferably, connector 130A is configured as a linear adjustment or latch and release connector operational in the x axis X and positioned between angle sections 104A and 104B. Preferably, second connector section 104A.2 of angle section 104A and second connector section 104B.2 of angle section 104B are configured as conduits with hollow passageway therethrough for insertion therein of a fastener, clasp, or latch mechanism, such as quick release pin 105A1/A2.

Preferably, quick release pin 105A1/A2 includes main body tube 105A, a bias mechanism, such as spring 105B, a rod, or pin, such as spindle 105C, and one or more balls 105D. Main body tube 105A preferably includes extension tube 105A.2 and alignment tube 105A.1 having a conduit or passageway 105A.4 therethrough with first access opening 105A.3 on one end of alignment tube 105A.1 and second access opening 105A.5 on one end of extension tube 105A.2 of body tube 105A. Preferably one or more small holes 105A.5 are drilled or formed in side wall 105A.6 of extension tube 105A.2, more specifically near one end or tip of extension tube 105A.2. One or more balls 105D are preferably positioned therein one or more small holes 105A.5, wherein one or more small holes 105A.5 are preferably configured to maintain one or more balls 105D in position to protrude through side wall 105A.6 of extension tube 105A.2 but not allow one or more balls 105D to pass all the way through one or more small holes 105A.5 and fall out. Spindle 105C preferably includes button 105C.1, spring support 105C.2, and spindle rod 105C.4. Preferably, spindle rod 105C.4 is passed through spring 105B, inserted in access opening 105A.3, further into passageway 105A.4, and further configured to contact or place pressure/force on the backside of one or more balls 105D to hold one or more balls 105D in one or more small holes 105A.5 of extension tube 105A.2. It is contemplated herein that spindle rod 105C.2 may contain a small section that is machined down to a smaller diameter or wedge, such as machined section 105C.3, where spindle rod 105C.2 contacts one or more balls 105D in the release position. Moreover, spindle rod 105C.4 includes first spindle end 105C.3, second spindle end 105C.6, and machined section 105C.5 of spindle rod 105C.2.

In use, when button 105C.1 on the end of spindle rod 105C.2 is pressed, such action compresses spring 105B between button 105C.1 and main body tube 105A, wherein spindle rod 105C.2 moves inward into passageway 105A.4 and enables one or more balls 105D to retract into extension tube 105A.2 from their seated positions into machined section 105C.5 of spindle rod 105C.2 (retracted position). In the retracted position, one or more balls 105D are preferably flush or slightly below the outside surface of extension tube 105A.2. When the button is released spring 105B provides pressure/force to pull spindle rod 105C.2 out of main body tube 105A and force one or more balls 105D to extend out of extension tube 105A.2 (extended position). In the extended position, one or more balls 105D are preferably in contact with receptacle 104A.7 of second connector section 104A.2 of angle section 104A releasably affixing angle section 104A to angle section 104B. It is contemplated herein that receptacle 104A.7 is preferably configured to receive extension tube 105A.2. In the extended and retracted position, one or more balls 105D of release pin 105A are configured to provide latch and release capability in the x axis X between angle sections 104A and 104B via connector 130A. It is contemplated herein that receptacle 104A.7 of second connector section 104A.2 may include one or more bored diameters to accommodate extension tube 105A.2 in its extended and retracted position to provide latch and release capability in the x axis X between angle sections 104A and 104B. It is further contemplated herein that receptacle 104A.7 of second connector section 104A.2 may include interior dimples or other configurations to catch one or more balls 105D when in their extended position to assist with latch capability in the x axis X between angle sections 104A and 104B. It is still further contemplated herein that other latch and release or the like mechanisms may be utilized herein.

Preferably, connector 130B (like connector 130C) is configured as a linear adjustment or latch and release connector operational in the x axis X and positioned between angle sections 114A and 114B. Preferably, second connector section 114A.2 of angle section 114A and second connector section 114B.2 of angle section 114B are configured as conduits with hollow passageway therethrough for insertion therein of a fastener, clasp, or latch mechanism, such as quick release pin 105A2. It is contemplated herein that quick release pin 105A may be utilized to provide latch and release capability in the x axis X between angle sections 114A and 114B.

It is recognized herein that connector 130A and connector 130B enable travel, adjustment, extension, latch, release, or retraction between angle sections 104A and 104B and angle sections 114A and 114B.

Preferably connector section 130C is positioned between rod 101A and angle sections 114A, connector section 130D is positioned between rod 101B and angle sections 114B, connector section 130E is positioned between rod 101B and angle sections 104B, and connector section 130F is positioned between rod 101A and angle sections 104A. For assembly, of connector section 130C first rod end 101A.1 of first rod section 101A is preferably inserted in first connector end 114A.3 configured to releasably and slidably connect first rod end 101A.1 of rod 101A thereto first connector section 114A.1 of angle section 114A. For assembly, of connector section 130D first rod end 101B.1 of first rod section 101B is preferably inserted in first connector end 114B.3 configured to releasably and slidably connect first rod end 101B.1 of rod 101B thereto first connector section 114B.1 of angle section 114B. For assembly, of connector section 130E second rod end 101B.2 of first rod section 101B is preferably inserted in first connector end 104B.3 configured to releasably and slidably connect second rod end 101B.2 of rod 101B thereto first connector section 104B.1 of angle section 104B. For assembly, of connector section 130F second rod end 101A.2 of first rod section 101A is preferably inserted in first connector end 104A.3 configured to releasably and slidably connect second rod end 101A.2 of rod 101A thereto first connector section 104A.1 of angle section 104A. It is contemplated herein that connector section 130C/D/E/F are preferably configured to enable travel along y axis Y, adjustment, positioning, or spacing therebetween angle sections 104A and 114A, and angle sections 104B and 114B. It is contemplated herein that connector section 130C/D/E/F may be affixed to angle section 114A, 114B, 104B, or 104A utilizing a weld, adhesive, mechanical connector, compression fitting or the like.

It is contemplated herein that stringer 100A may include a single axis of adjustment or telescope, such as along the x axis X or y axis Y or alternatively a multi axis adjustment or telescope, such as along the x axis X and y axis Y.

It is further contemplated herein that connector 130A/B/C/D/E/F of stringer 100A may include inner rod that is slidably longitudinally received within a hollow outer rod and that each end of a rod may be interchanged from inner to outer.

It is still further contemplated herein that connector 130A/B/C/D/E/F of stringer 100A may be interchanged.

It is still further contemplated herein that connector 130A/B/C/D/E/F of stringer 100A may include one or more expand and contract sections or slidable sections to enable x axis X and/or y axis Y parallel adjustment or spacing of the rods that form stringer 100A.

Referring now to FIG. 4.1 an exemplary surgical instrument I, such as a hemostat having moveable shank S1 and shank S2, which preferably includes a pair of opposing first jaw member J1 and second jaw members J2, jaw members, wherein at least one of the jaw members is movable relative to the other. Such jaw members may be pivotable about pivot point P, within box lock B, between first open position O in which the jaw members are disposed in a spaced relation relative to one another, and second closed position C in which the jaw members are configured to grasp or clamp something therebetween, such as tissue, or the like. Moreover, opposing first jaw member J1 and second jaw members J2 may be locked or held in position by a lock such as ratchet lock L preferably positioned on an extension stem or support member such as shank S1 and shank S2 between the two ring handles R. In use, for example a user positions their thumb in first ring handle R1 and their index or middle finger within second ring handle R2. By a user opening and closing their thumb and index or middle finger this causes first ring handle R1 and second ring handle R2 to move apart (first open position O) and together (second closed position C), accordingly. The movements of first ring handle R1 and second ring handle R2 causes shank S1 and shank S2 to pivot about pivot point P which results in first jaw member J1 and second jaw members J2 to likewise pivot about pivot point P between first open position O and second closed position C.

Further, surgical instruments I may include hemostats, forceps, clamps, scalpels, scissors, picks, retractors, hooks, clips, pliers, punches, curettes, specula and the like, which are generally of high precision and intricate construction and come in a variety of types, shapes and sizes, all of which may be used during a particular surgical procedure. A variety of surgical tools exist for each category of instruments. For example, considering only forceps, they come straight, left curved, right curved, serrated, cupped, etc. In addition, a range of medical, dental and veterinary tools have been developed for each discipline, such as in medicine sub-categories of surgical procedures include anesthesia, cardio, dermatology, ear nose & throat, hand (specific limbs), facial, ob/gyn, orthopedic and the like each discipline having a variety of specialty and common surgical instruments. Over the years, surgical procedures along with the type and quantity of surgical instruments used in a given procedure have become predominantly standardized. Many of the above-mentioned instruments are scissor action instruments, having a pair of ring handles R that are connected through a pivot P to working moveable members shank S1 and shank S2. Preferably, lever, extension or support members such as shank S typically include ring handles R at the ends thereof to facilitate the opening and closing of shank S1 and shank S2 connected to first jaw member J1 and second jaw members J2.

Referring now to FIG. 4.2 an exemplary embodiment of a plurality of surgical instruments I strung together by stringer 100A. Preferably rod 101A and rod 101B of stringer 100A are positioned through first ring handle R1 and second ring handle R2 of one or more surgical instruments I to group surgical instruments I in sequential order along y axis Y. Moreover, one exemplary function of the extension and retraction capability of connector 130C/F (shown in FIG. 3) and 130D/E is to enable stringer 100A to accommodate additional (expansion) or fewer (retraction) numbers of surgical instruments I along y axis Y. Such extension and retraction maintains a tight y axis Y fit around ring handles R of the group surgical instruments I and holds the group surgical instruments I in an erect position. Such erect position, space between instruments, and organization of the group surgical instruments I enables shortened time to identify, clean (whether pre-wash, pressure washing or the like), sort, count, group, and sterilize surgical instrument I. Moreover, such erect position, space between instruments, and organization of the group surgical instruments I reduces instrument damage when transporting, stacking, sorting, inspecting, and counting, and additionally when positioning on a sorting table for a technician to inspect, count, and sort. Still further, such extension and retraction of connector 130C/F (shown in FIG. 3) and 130D/E enables stringer 100A to adjust and accommodate a variety of sizes of surgical instruments I1/I2 and numbers or groups of surgical instruments I. It is contemplated herein that first peg 104A.8, second peg 104B.8, third peg 114A.8, and fourth peg 114B.8 may be utilized to raise first ring handle R1 and second ring handle R2 of one or more surgical instruments I above a surface or plug or insert into a holed surface.

Procedurally the surgical instruments I should be strung post-surgery when in their aligned position on the surgical instrument roll by feeding stringer 100A through first ring handle R1 and second ring handle R2. Thereafter the surgical instruments I are preferably handled as a group of surgical instruments I bound together by stringer 100A through the multi-step sorting, identifying, grouping, cleaning and sterilization process. Such bundling of surgical instruments I preferably helps to protect surgical instruments I from damage when transported, stacked one on the other as well as when the surgical instruments are emptied out on a sorting table (no longer required) for a technician to inspect, count, and sort. Such handling may scratch, bend and may even break the surgical instruments resulting in increased cost to replace such instruments, which are often delicate and expensive. Moreover, such damage to the surgical instruments reduces the life expectancy of the surgical instruments resulting in increased medical costs to replace the surgical instruments. Furthermore, if such damaged surgical instruments are accidentally returned to the operating room, such surgical procedures may be delayed or cancelled due to non-functioning surgical instruments causing lost revenue for the surgery center and an upset surgical team and patients in queue.

Moreover, one exemplary function of the release and latch capability of connectors 130A and 130B (shown in FIG. 3) is to enable stringer 100A to accommodate surgical instruments I in an open position O and upright. Such release and latch of connector 130A and 130B (shown in FIG. 3) maintains x axis X spacing between first ring handle R1 and second ring handle R2 of the group surgical instruments I. Such movement of first ring handle R1 and second ring handle R2 causes shank S1 and shank S2 to pivot about pivot point P which results in first jaw member J1 and second jaw members J2 to likewise pivot about pivot point P. Preferably stringer 100A holds the group surgical instruments I in an erect position with opposing first jaw member J1 and second jaw members J2 held in open position O. Such open position O, spacing between instruments, and organization of the group surgical instruments I enables more thorough cleaning and sterilization of surgical instruments I. In addition, maintaining such open position O between first jaw member J1 and second jaw members J2 preferably reduces the time to sort, identify, inspect, group, clean and sterilize the group surgical instruments I. Moreover, such open position O of the plurality of surgical instruments I strung together by stringer 100A reduces the number of sharps being sent to central sterile and the reduction of accidents associated with needle/sharps injuries retained in a surgical instrument I or hidden in an un organized cluster of surgical instruments I. Such erect position, spacing between instruments, and organization of the group surgical instruments I enables shortened time to identify, clean (whether pre-wash, pressure washing or the like), sort, count, group, and sterilize surgical instrument I. Still further, such release and latch of connector 130A and 130B (shown in FIG. 3) enables stringer 100A to adjust and accommodate a variety of sizes of surgical instruments I and groups of surgical instruments I.

Referring now to FIG. 5.1 there is illustrated a perspective view of an example embodiment box like tray bottom and lid surgical instrument support tray system 10 with exemplary adjustable stringer 100 position or affixed thereon. Preferably, surgical instrument support tray system 10 includes a container or basket and lid, such as tray bottom 220 and tray top 320. Tray bottom 220 and tray top 320 are preferably formed of a suitable material, stainless steel, aluminum, metal, metal alloys, shape memory alloys, carbon fibers, ceramic, and includes chrome or other plated metals or coated metal and anodizing or the like, capable of providing structure to tray bottom 220 and tray top 320. Preferably, the material includes other suitable characteristics, such as durability, rigidity, stain-resistance, bacteria-resistant, light weight, chemical inertness, oxidation resistance, ease of workability, color coding, or other beneficial characteristic understood by one skilled in the art.

Referring now to FIG. 5.2.1 there is illustrated a perspective view of an example embodiment tray bottom 220. Preferably, tray bottom 220 may be configured as a basket-like housing or enclosure in which surgical instruments I may be positioned, sterilized, transported and stored for later use. Tray bottom 220 comprises four generally perpendicular, upwardly projecting, continuous planar member(s), surface(s) or side(s) such as such as side walls 222, 223, 224, 225 and bottom 226 arranged preferably as a rectangle or square and having an open top box. Side walls 222-225 preferably define a generally open top having an upper perimeter 227.

It is contemplated herein that one or more sides walls 222, 223, 224, 225 and bottom 226 may be formed from a wire grid construction.

It is further contemplated herein that tray bottom 220 may include a variety of shapes and sizes to accommodate a variety of surgical instruments I.

Referring again to FIG. 5.2.1, preferably side walls 222, 223, 224, 225 and bottom 226 may be formed or configured with a plurality or set of holes such as apertures 240 to enable steam or other sterilant to flow through apertures 240 formed in side walls 222, 223, 224, 225 and bottom 226 and permeate the entire interior of tray bottom 220. Furthermore, such sterilant may pass up, under and over the surgical instruments I positioned in tray bottom 220, thus ensuring effective sterilization.

Preferably, tray bottom 220 includes two or more wire handles such as handle wire 230 configured generally in a u-shape. Handle wire 230 is preferably positioned approximate an interior side of one of side walls 222, 223, 224, or 225 (preferably 223 and 225) and removably affixed thereto and configured to enable swivel movement of handle wire 230 about a plate such as handle retainer plate 232. At least two handle retainer plates 232 are preferably affixed to side walls 223 and 225 by an attachment device such as machined screw 234 positioned through machined apertures 236 configured in side walls 223 and 225. Handle wires 230 are preferably affixed to side walls 223 and 225 to facilitate the lifting, carrying and positioning of tray bottom 220.

Furthermore, any of side walls 222, 223, 224, 225 and bottom 226 may include an identifying legend such as indicia 231 to enable identification of the surgical instruments I contained therein or the surgical procedure identified with the set or group of surgical instruments I contained within tray bottom 220, surgical kit identification, dates of sterilization, dates of expiration, model number, serial number, ownership and the like.

Referring now to FIG. 5.2.2 there is illustrated a perspective view of an example embodiment surface, lid or cover, such as tray top 320 of the surgical instrument support tray system 10. Preferably, tray top 320 may be configured as a box top, cover, closure or lid for tray bottom 220 in which surgical instruments I may be positioned, removably affixed thereto, sterilized, transported and stored for later use. Tray top 320 comprises four generally perpendicular, downwardly projecting, continuous, planar member(s), surface(s) or side(s) arranged preferably as a rectangle or square, such as side walls 322-325. Side walls 322-325 preferably define a top having perimeter 227 configured to engage, surround, or friction fit side walls 222-225 of tray bottom 220 to form an enclosure in which surgical instruments I may be positioned, removably affixed thereto, sterilized, transported and stored for later use. It is contemplated herein that tray bottom 220 and tray top 320 may include a latch mechanism to secure tray bottom 220 and tray top 320 to one another. Furthermore, any of side walls 322, 323, 324, 325 and/or top 326 may be configured as a support member for surgical instruments I, such as top 326.

Likewise, side walls 322, 323, 324, 325 and top 326 may be formed or configured with a plurality or set of holes such as apertures 340 to enable steam or other sterilant to flow through apertures 340 formed in side walls 322, 323, 324, 325 and top 326 and permeate the entire interior of tray top 320 and into the interior of tray bottom 220. Furthermore, such sterilant may pass down through tray top 320 and over the surgical instruments I positioned in tray bottom 220, thus ensuring effective sterilization.

It is contemplated herein that tray bottom 220 and tray top 320 may be configured in shapes other than square and rectangle provided such configuration enables sterilization, transport and storage for later use of surgical instruments I.

Referring again to FIG. 5.2.2, preferably top 326 of tray top 320 includes regularly spaced columns or rows of a plurality or set of furrows, trenches, channel or troughs, such as valleys 650 formed therein top 326. Valleys 650, such as first valley 651 and second valley 652, are formed as a pair of columns in top 326 of tray top 320, and are preferably configured as a furrows, trenches, channel or troughs shape positioned parallel to side walls 323 and 325, into which portions of surgical instrument I, preferably ring handles R may be held or positioned. Preferably, ring handles R may be positioned and/or held in a desired and evenly spaced position therein valleys 650 preventing surgical instrument I from coming into contact with one another, intermingling, and enabling easy identification, cleaning, sorting, counting, and grouping of surgical instruments I. Valleys 650 are preferably formed in sets of two to accommodate stringer 100 and a group of ring handles R of surgical instruments I bound together by stringer 100. Moreover, one or more pins, plugs, screws, rivets, bolts, clips or other fastener, such as stringer attachment device 700 may be utilized to affix stringer 100 and/or a group of surgical instruments I bound together by stringer 100 to tray top 320. It is contemplated herein that stringer attachment device 700, more specifically first attachment device 702 and second attachment device 704, may affix stringer 100 or a group of surgical instruments I bound together by stringer 100 to one or more apertures 340 in side walls 322, 323, 324, 325 and/or top 326, especially apertures 340 adjacent perimeter 227.

Referring now to FIG. 5.3.1 there is illustrated a top view of an example embodiment lid or cover, such as tray top 320 of the surgical instrument support tray system 10. Preferably top 326 of tray top 320 includes regularly spaced S columns or rows of a plurality of valleys 650, such as first valley 651, second valley 652, third valley 653 and the like, formed therein top 320. Valleys 650 are preferably spaced S distance apart to accommodate, cup and support ring handles R of surgical instrument I therein. In addition, valleys 650 are preferably spaced S distance apart to maintain surgical instrument I in open position O, shown in FIG. 4. Preferably top 326, includes valleys 650, as a pair, such as first valley 651 and second valley 652, are formed as a pair of columns, and are preferably configured as a furrows, trenches, channel or troughs shape positioned parallel to side walls 323 and 325, into which portions of surgical instrument I, such as ring handles R may be positioned or held. Preferably, ring handles R may be positioned and/or held in a desired and evenly spaced position therein valleys 650 in top 326 preventing surgical instrument I from coming into contact with one another, intermingling, and enabling easy identification, cleaning, sorting, counting, and grouping of surgical instruments I.

Referring now to FIG. 5.3.3 there is illustrated a cross sectional side view along AA of tray top, such as tray top 320 of the surgical instrument support tray system 10. Preferably top 326 shown from side wall 324, includes valleys 650, as a plurality of pairs, such as first valley 651 and second valley 652 (first pair) and third valley 653 and fourth valley 654 (second pair), each formed as a pair into which portions of surgical instrument I, preferably one or more sets of ring handles R may be positioned or held preventing surgical instrument I from coming into contact with one another, intermingling, and enabling easy identification, cleaning, sorting, counting, and grouping of surgical instruments I.

Referring now to FIG. 5.3.2 there is illustrated a side cross sectional view of tray top 320 along line A-A showing cross sectional of surface 326 of the surgical instrument support tray system 10. Preferably, valleys 650, such as second valley 652, third valley 653 and the like, formed therein top 320. Preferably, valleys 650, such as second valley 652 includes a curved, arced or bent surface, such as second contoured surface 662 and end edge 664, and third valley 653 includes third contoured surface 663 and end edge 664. Moreover, therebetween and on each side of valleys 650, such as second valley 652 and third valley 653 there is shown cross sectional of surface 326. Preferably contoured surfaces, such as second contoured surface 662 and third contoured surface 663 are formed in top 320 and spaced S distance apart to position or hold ring handles R in a desired and evenly spaced position when positioned therein valleys 650 to prevent surgical instrument I from coming into contact with one another, intermingling, and enabling easy identification, cleaning, sorting, counting, and grouping of surgical instruments I. It is contemplated herein that second contoured surface 662 and third contoured surface 663 may be configured or formed as polygon, curved or the like to conform to, position, or hold ring handles R of surgical instrument I.

Manufacture

Preferably, tray bottom 220, tray top 320 and contoured surface 662 and contoured surface 663 of valleys 650 are formed as follows: a turret machine is preferably utilized to punch all apertures 240 and 340 in a stock sheet of aluminum or stainless steel and to cut outside perimeter shape, such as perimeter 227. Next, "brake press" (a large hydraulic press machine) is preferably used to press one or more valleys 650 into surface 326 of tray top 320. Next, the brake press is preferably utilized to form side walls 322, 323, 324, 325 of tray top 320. It is contemplated herein that large volumes of production of tray top 320 may be formed using automated processes known to one of ordinary skill in the art. For example, preferably utilizing a larger "die" shaped to press all apertures 240 and 340 in a stock sheet of aluminum or stainless steel and to cut outside perimeter shape, such as perimeter 227 in one hit/press. Next, a similar press is preferably utilized to press one or more valleys 650 into surface 326 of tray top 320 and to form side walls 322, 323, 324, 325 of tray top 320 in one hit/press.

It is contemplated herein that tray bottom 220 may be configured or formed with one or more valleys 650, similar to tray top 320, formed in bottom 226 of tray bottom 220, to accommodate ring handles R may, which may be positioned and held in a desired and evenly spaced position preventing surgical instrument I from coming into contact with one another, intermingling, and enabling easy identification, cleaning, sorting, counting, and grouping of surgical instruments I. Referring again to FIG. 5.3.2 there is illustrated a side cross sectional view of tray bottom 220 showing cross sectional surface 326 of the surgical instrument support tray system 10.

Referring now to FIGS. 5.4.1 and 5.4.2 there is illustrated a top and cross sectional view of an example embodiment tray bottom 220. Preferably tray bottom 220 includes one or more fastener, hanger, peg, or arm, such as thumb screw 252 and 254, more specifically thumb screws 252A, 252B, 252C, and 252D for insertion in apertures 242A, 242B, 242C, and 242D (shown in FIG. 5.2) of side walls 222 and thumb screws 254A, 254B, 254C, and 254D for insertion in apertures 244A, 244B, 244C, and 244D (shown in FIG. 5.2) of side walls 224. Thumb screw 252 and 254 are preferably inserted in apertures 242A, 242B, 242C, and 242D (shown in FIG. 5.2) in side walls 222 and in apertures 244A, 244B, 244C, and 244D (shown in FIG. 5.2) in side walls 224, respectively, and utilized to support an inner tray, such as surgical instrument support tray system 10.1. It is contemplated herein that surgical instrument support tray system 10.1 may be color coordinated and/or grouped within surgical instrument support tray system 10 for easy identification of assemblies for specific surgical specialties. Preferably, surgical instrument support tray system 10.1 may be configured or utilized to support specialty, random, non-ring handled surgical instruments or other surgical instruments. It is contemplated that side walls 222 and 224 may include one or more parallel first set of thumb screws 252A, 252B, 252C, and 252D and one or more parallel second set of thumb screws 254A, 254B, 254C, and 254D or the like to provide support and accommodate a variety of configured inner tray(s), such as surgical instrument support tray system 10.1.

Referring again to FIG. 5.5, preferably top 326 of tray top 320 includes regularly spaced columns or rows of a plurality or set of furrows, trenches, channel or troughs, such as valleys 650 formed therein top 326. Valleys 650, such as first valley 651 and second valley 652, are formed as a pair of columns in top 326 of tray top 320, and are preferably configured as a furrows, trenches, channel or troughs shape positioned parallel to side walls 323 and 325, into which portions of surgical instrument I, preferably ring handles R may be held or positioned. Preferably, ring handles R may be positioned and/or held in a desired and evenly spaced position therein valleys 650 preventing surgical instrument I from coming into contact with one another, intermingling, and enabling easy identification, cleaning, sorting, counting, and grouping of surgical instruments I. Valleys 650 are preferably formed in sets of two to accommodate stringer 100A and a group of ring handles R of surgical instruments I bound together by stringer 100A. Moreover, one or more pegs, such as that first peg 104A.8, second peg 104B.8, third peg 114A.8, and fourth peg 114B.8 may be utilized to releasably connect or plug stringer 100A and/or a group of surgical instruments I bound together by stringer 100A to tray top 320. It is contemplated herein that one or more pegs, more specifically first peg 104A.8, second peg 104B.8, third peg 114A.8, and fourth peg 114B.8, may releasably connect stringer 100A or a group of surgical instruments I bound together by stringer 100A to one or more apertures 340/340A in side walls 322, 323, 324, 325 and/or top 326, especially apertures 340 adjacent perimeter 227 of top 326.

It is contemplated herein that cover or grommet 504A and grommet 514A may be inserted in one or more apertures 340/340A and configured to releasably affix or hold one or more pegs, more specifically first peg 104A.8 of angle section 104A and third peg 114A.8 of angle section 114A to prevent angle section 104A and angle section 114A (stationary side of stringer 100A) from dislodging, during use, from apertures 340/340A in top 326.

Referring now to FIG. 6.1 there is illustrated a perspective view of an example embodiment of a surgical instrument support tray system 10 with exemplary adjustable stringers 100 shown adjusted in two positions affixed to tray top 320 of the surgical instrument support tray system 10. Preferably, surgical instrument support tray system 10 includes tray bottom 220 and tray top 320, and tray top 320 includes a plurality of regularly spaced valleys 650 formed therein top 326, such as first valley 651, second valley 652, third valley 653, fourth valley 654, fifth valley 655, sixth valley 656, seventh valley 657, and eighth valley 658. Preferably, stringer 100A is adjusted, positioned, or expand and contract along slidable coupler sections 130A/B/C/D of stringer 100A to enable x axis X and/or y axis Y parallel adjustment or spacing of the rods that form stringer 100A to be positioned approximate first valley 651 and third valley 653 of tray top 320. Alternatively, stringer 100B is adjusted, positioned, or expand and contract along slidable coupler sections 130A/B/C/D of stringer 100B to enable x axis X and/or y axis Y parallel adjustment or spacing of the rods that form stringer 100B to be positioned approximate fifth valley 655 and sixth valley 656 of tray top 320. It is contemplated herein that slidable coupler sections 130A/B/C/D of stringer 100A/B may be adjusted or expand and contract along slidable coupler sections 130A/B/C/D of stringer 100A/B to enable x axis X and/or y axis Y parallel adjustment, positioning, or spacing of the rods that form stringer 100A/B to be positioned approximate a pair or a plurality of valleys 650 of tray top 320.

It is contemplated herein that stringer 100A/B may be color coordinated and/or grouped within inner tray, such as surgical instrument support tray system 10.1 and/or surgical instrument support tray system 10 for easy identification of assemblies for specific surgical specialties.

Referring now to FIG. 6.1A there is illustrated a perspective view of an example embodiment of tray top 320 with exemplary stringers 100A shown adjusted in two positions affixed to tray top 320. Preferably, tray top 320 includes a plurality of regularly spaced valleys 650 formed therein top 326, such as first valley 651, second valley 652, third valley 653, fourth valley 654, fifth valley 655, sixth valley 656, seventh valley 657, and eighth valley 658. Preferably, stringer 100A1 is latched, adjusted, positioned, released, or expands and contracts along connector sections 130A/B/C/D/E/F of stringer 100A to enable x axis X and/or y axis Y parallel adjustment or spacing of the rods that form stringer 100A1 and to be positioned approximate first valley 651 and second valley 652 of tray top 320. Alternatively, stringer 100A2 is latched, adjusted, positioned, released, or expands and contracts along connector sections 130A/B/C/D/E/F of stringer 100A2 to enable x axis X and/or y axis Y parallel adjustment or spacing of the rods that form stringer 100A2 to be positioned approximate seventh valley 657 and eighth valley 658 of tray top 320. It is contemplated herein that connector sections 130A/B/C/D/E/F of stringer 100A1/A2 may be latched, released, adjusted or expand and contract along connector sections 130A/B/C/D/E/F of stringer 100A1/A2 to enable x axis X and/or y axis Y parallel adjustment, positioning, or spacing of the rods that form stringer 100A1/A2 to be positioned approximate a pair or a plurality of valleys 650 of tray top 320. It is contemplated herein that one or more pegs, more specifically first peg 104A.8, second peg 104B.8, third peg 114A.8, and fourth peg 114B.8, may be releasably positioned or inserted therein apertures 340/340A to affix stringer 100A1/A2 or a group of surgical instruments I bound together by stringer 100A1/A2 to one or more apertures 340/340A in side walls 322, 323, 324, 325 and/or top 326, especially apertures 340/340A adjacent perimeter 227 of top 326.

It is contemplated herein that stringer 100A1/A2 may be color coordinated and/or grouped within inner tray, such as surgical instrument support tray system 10.1 and/or surgical instrument support tray system 10 for easy identification of assemblies for specific surgical specialties.

It is further contemplated herein that cover or grommet 504A and grommet 514A may be inserted in one or more apertures 340/340A of top 326 and configured to releasably affix or hold one or more pegs, more specifically first peg 104A.8 of angle section 104A and third peg 114A.8 of angle section 114A of stringer 100A1 and 180 degree rotated first peg 104A.8 of angle section 104A and third peg 114A.8 of angle section 114A of stringer 100A2; thus, to prevent angle section 104A and angle section 114A (stationary side of stringer 100A1/A2) from dislodging, during use, from apertures 340/340A in top 326.

Referring now to FIG. 6.2 there is illustrated a perspective view of an example embodiment of a surgical instrument support tray system 10 with a plurality of surgical instrument sets I held in a vertical position by exemplary adjustable stringers 100A/B affixed or positioned approximate to tray top 320 of surgical instrument support tray system 10. Preferably, surgical instrument support tray system 10 includes tray bottom 220 and tray top 320, and tray top 320 includes a plurality of regularly spaced valleys 650 formed therein top 326. For example, stringer 100A positions and holds ring handle R1 in valley 651 and positions and holds ring handle R2 in valley 653 of tray top 320 for surgical instruments IA. Such positioning of surgical instruments IA preferably maintains opposing first jaw member J1 and second jaw members J2 in open position O for cleaning and sterilization purposes. Furthermore, such positioning of surgical instruments IA preferably maintains the instruments in a desired and evenly spaced position preventing them from coming into contact with one another, intermingling, and enabling easy identification, cleaning, sorting, counting, and grouping of surgical instruments IA.

As an alternative example, stringer 100B positions and holds ring handle R1 in valley 655 and positions and holds ring handle R2 in valley 656 of tray top 320 for surgical instruments IB. Such positioning of surgical instruments IB preferably maintains opposing first jaw member J1 and second jaw members J2 of surgical instruments IB in open position O for cleaning and sterilization purposes. Furthermore, such positioning of surgical instruments IB preferably maintains the instruments in a desired and evenly spaced position preventing them from coming into contact with one another, intermingling, and enabling easy identification, cleaning, sorting, counting, and grouping of surgical instruments IB.

Moreover, one or more stringer attachment device 700 may be utilized to affix stringer 100A/B and/or a group of surgical instruments I bound together by stringer 100A/B to tray top 320. It is contemplated herein that stringer attachment devices 700, more specifically first stringer attachment devices 700A and second stringer attachment devices 700B, may affix stringer 100A/100B or a group of surgical instruments I bound together by stringer 100A/B to one or more apertures 340 in top 326, especially apertures 340 adjacent perimeter 227.

Referring now to FIG. 6.2A there is illustrated a perspective view of an example embodiment of tray top 320 with exemplary stringers 100A1/A2 shown adjusted in two positions affixed to tray top 320 with a plurality of surgical instrument sets I held in a proximately vertical position by exemplary stringers 100A1/A2 affixed, connected, or positioned approximate to tray top 320. Preferably, tray top 320 includes a plurality of regularly spaced valleys 650 formed therein top 326. For example, stringer 100A1 positions and holds ring handle R1 in first valley 651 and positions and holds ring handle R2 in second valley 652 of tray top 320 for surgical instruments IA. Such positioning of surgical instruments IA preferably maintains opposing first jaw member J1 and second jaw members J2 in open position O for cleaning and sterilization purposes. Furthermore, such positioning of surgical instruments IA preferably maintains the instruments in a desired and evenly spaced position preventing them from coming into contact with one another, intermingling, and enabling easy identification, cleaning, sorting, counting, and grouping of surgical instruments IA.

As an alternative example, stringer 100A2 positions and holds ring handle R1 in valley 657 and positions and holds ring handle R2 in valley 658 of tray top 320 for surgical instruments IB. Such positioning of surgical instruments IB preferably maintains opposing first jaw member J1 and second jaw members J2 of surgical instruments IB in open position O for cleaning and sterilization purposes. Furthermore, such positioning of surgical instruments IB preferably maintains the instruments in a desired and evenly spaced position preventing them from coming into contact with one another, intermingling, and enabling easy identification, cleaning, sorting, counting, and grouping of surgical instruments IB.

Moreover, one or more pegs, more specifically first peg 104A.8, second peg 104B.8, third peg 114A.8, and fourth peg 114B.8, may be positioned, connected, or inserted in apertures 340/340A to releasably affix stringer 100A1/A2 or a group of surgical instruments IA/IB bound together by stringer 100A1/A2 to one or more apertures 340/340A in top 326, especially apertures 340/340A adjacent perimeter 227.

Referring now to FIG. 6.3A there is illustrated a perspective view of an example embodiment of tray top 320 with exemplary stringer 100A shown unlatched in two positions, such as connector sections 130A/B and stringer 100A is further affixed to tray top 320 with a plurality of surgical instrument sets I held in a proximately vertical position by exemplary stringers 100A affixed or positioned approximate to tray top 320. Preferably, stringer 100A is unlatched in two positions, such as connector sections 130A/B to enable assembly A1, such as rod 101A, and angle sections 104A/114A to be releasably positioned, affixed or inserted by pegs 104A.8/114A.8 to apertures 340/340A of tray top 320 and to be positioned in regularly spaced valleys 650, such as valley 651, and assembly A2, such as rod 101B, and angle sections 104B/114B to be releasably positioned, affixed or inserted by pegs 104B.8/114B.8 to apertures 340/340A of tray top 320 and to be positioned in any regularly spaced valleys 650, such as valley 654. Such configuration enables longer spanked surgical instrument sets I, such as shank S1 and shank S2, to be positioned with opposing first jaw member J1 and second jaw members J2 of surgical instruments I in wide open position O for better cleaning and sterilization purposes and to enable easy identification, pressure washing, sorting, counting, and grouping of surgical instruments I. It is contemplated herein that assembly A1, such as rod 101A, and angle sections 104A/114A and/or assembly A2, such as rod 101B, and angle sections 104B/114B; may be affixed by receptacle 104A.7 of second connector end 104A.5 of angle sections 104A; receptacle 114A.7 of second connector end 114A.5 of angle sections 114A; protrusion 104B.7 of second connector end 104B.5 of angle sections 104B; and/or protrusion 114B.7 of second connector end 114B.5 of angle sections 114B; respectively, configured to preferably match, fit, affix, insert, or latch apertures 340/340A of tray top 320, especially apertures 340/340A adjacent perimeter 227. Such configuration enables longer spanked surgical instrument sets I, such as shank S1 and shank S2, to be positioned with opposing first jaw member J1 and second jaw members J2 of surgical instruments I in wide open position O for better cleaning and sterilization purposes and to enable easy identification, pressure washing, sorting, counting, and grouping of surgical instruments I.

It is further contemplated that receptacle 104A.7 and receptacle 114A.7 may releasably affix to a pin or peg (similar to peg 104A.8) formed in tray top 320.

It is further contemplated herein that assembly A1 may be positioned in any of regularly spaced valleys 650 and assembly A2 may be positioned in any other regularly spaced valleys 650.

Referring now to FIG. 6.4A there is illustrated a perspective view of an example embodiment of tray top 320 with exemplary stringer 100A shown unlatched in two positions, such as connector sections 130A/B (shown in FIG. 3) and stringer 100A is further releasably affixed to tray top 320 with a plurality of surgical instrument sets IA/B held in a proximately vertical position by exemplary stringers 100A releasably affixed or positioned approximate to tray top 320. Preferably, stringer 100A is unlatched in two or more positions, such as connector sections 130A/B (shown in FIG. 3) and at least slidably adjusted by connector sections 130C/F (shown in FIG. 3) of stringer 100A to enable assembly A1, such as rod 101A, and angle sections 104A/114A (shown in FIG. 6.3A) to be releasably affixed by pegs 104A.8/114A.8 (shown in FIG. 3) to apertures 340/340A of tray top 320 and to be positioned in regularly spaced valleys 650, such as valley 651, and at least slidably adjusted by connector sections 130D/E (shown in FIG. 3) of stringer 100A to enable assembly A2, such as rod 101B, and angle sections 104B/114B (shown in FIG. 3) to be releasably affixed by pegs 104B.8/114B.8 (shown in FIG. 3) to apertures 340/340A of tray top 320 and to be positioned in regularly spaced valleys 650, such as across valleys 653 and 654.

Such configuration enables shorted shanked surgical instrument sets I, such as shank S1 and shank S2 of surgical instruments IA and longer shanked surgical instrument sets IB, such as shank S1 and shank S2 of surgical instruments IB, to be to be grouped on a common stringer 100A and positioned with opposing first jaw member J1 and second jaw members J2 of surgical instruments IA/B in wide open position O for better cleaning and sterilization purposes and to enable easy identification, pressure washing, sorting, counting, and grouping of surgical instruments IA/B. It is further contemplated herein that assembly A1, such as rod 101A, and angle sections 104A/114A and/or assembly A2, such as rod 101B, and angle sections 104B/114B (shown in FIG. 6.3A) may be affixed by receptacle 104A.7 of second connector end 104A.5 of angle sections 104A; receptacle 114A.7 of second connector end 114A.5 of angle sections 114A; protrusion 104B.7 of second connector end 104B.5 of angle sections 104B; and/or protrusion 114B.7 of second connector end 114B.5 of angle sections 114B; (shown in FIG. 3) respectively, configured preferably to match, fit, affix, insert, or latch any of apertures 340/340A of tray top 320, whether apertures 340/340A are adjacent perimeter 227 or positioned interior to perimeter 227. Such configuration enables shorter shanked surgical instrument sets I, such as shank S1 and shank S2 of surgical instruments IA and longer shanked surgical instrument sets IB, such as shank S1 and shank S2 of surgical instruments IB to be positioned with opposing first jaw member J1 and second jaw members J2 of surgical instruments IA/B in wide open position O for better cleaning and sterilization purposes and to enable easy identification, pressure washing, sorting, counting, and grouping of surgical instruments IA/B. Moreover, stringer 100A accommodates shorter shanked surgical instrument sets IA and longer shanked surgical instrument sets IB, on one stringer 100 in wide open position O for better cleaning and sterilization purposes and to enable easy identification, pressure washing, sorting, counting, and grouping of surgical instruments IA/B.

Referring now to FIG. 7.1 there is illustrated an exploded perspective view of the attachment device of FIG. 5.2.2. Preferably, stringer attachment device 700 includes pan head bolt 780, coil spring 760, cylindrical spacer 740, clip 720 and threaded end cap 710. One or more stringer attachment devices 700 may be utilized to affix a portion of stringer 100 and/or a group of surgical instruments I bound together by stringer 100 to tray top 320.

It is contemplated herein that stringer attachment device 700 includes other configurations of attachment devices known to one of ordinary skill in the art.

Referring now to FIG. 7.2 there is illustrated a perspective view of an exemplary alternate stringer attachment device 801. Referring now to FIG. 7.2.2 there is illustrated a perspective view of an alternate stringer attachment device 801 that preferably includes releasably friction clip, snap-in clasp, or channel, such as trough 802 having first trough wall 804 and second trough wall 806, base 807, and pin, dowel, threaded bolts, screws, pine tree plugs or the like, such as pegs 808. Referring now to FIG. 7.2.3 there is illustrated a side view of an alternate stringer attachment device 801 having pegs 808, base 807, and first trough wall 804. Referring now to FIG. 7.2.1 there is illustrated a perspective view of one or more exemplary alternate stringer attachment device 801 in combination with stringer attachment device 700 in use. Preferably, alternate stringer attachment device 801 is positioned on top 326 of tray top 320 and aligned with apertures 340 in top 326, especially apertures 340 adjacent perimeter 227. Moreover, pegs 808 are preferably pushed through apertures 340 adjacent perimeter 227 and friction fit therein to top 326 or secured thereto top 326 by nuts or other attachment mechanism know to one of ordinary skill. One or more alternate stringer attachment device 801 may be utilized to affix or frictionally secure a portion of stringer 100 and/or a group of surgical instruments I bound together by stringer 100 to tray top 320.

Procedure

Referring again to FIG. 7.2.1 there is illustrated either stringer attachment device 700 or alternate stringer attachment devices 801 affixed to tray top 320, which may be additionally utilized to position and frictionally affix one end, side, rod or section of stringer 100, such as slidable coupler section 130A, of stringer 100 to tray top 320 while the other end, of stringer 100 is swung or hinged up or vertically positioned with rods 102A and 102B perpendicular or adjacent to top 326 of tray top 320. Moreover, slidable coupler sections 130C and 130D may be temporarily removed to enable stringing of ring handles R of surgical instrument I onto rods 102A and 102B. Once ring handles R of surgical instrument I have preferably been strung onto rods 102A and 102B slidable coupler sections 130C and 130D may be reattached to stringer 100 to group together surgical instruments I and stringer 100. Preferably, stringer 100 is adjusted or expand and contract along connector 130A/B/C/D/E/F of stringer 100 to position stringer 100 approximate valleys 650 and thereafter the other end, such as connector 130B of stringer 100 is re-affixed to either stringer attachment device 700 or alternate stringer attachment devices 801, as shown in FIG. 6.

Figure 8:
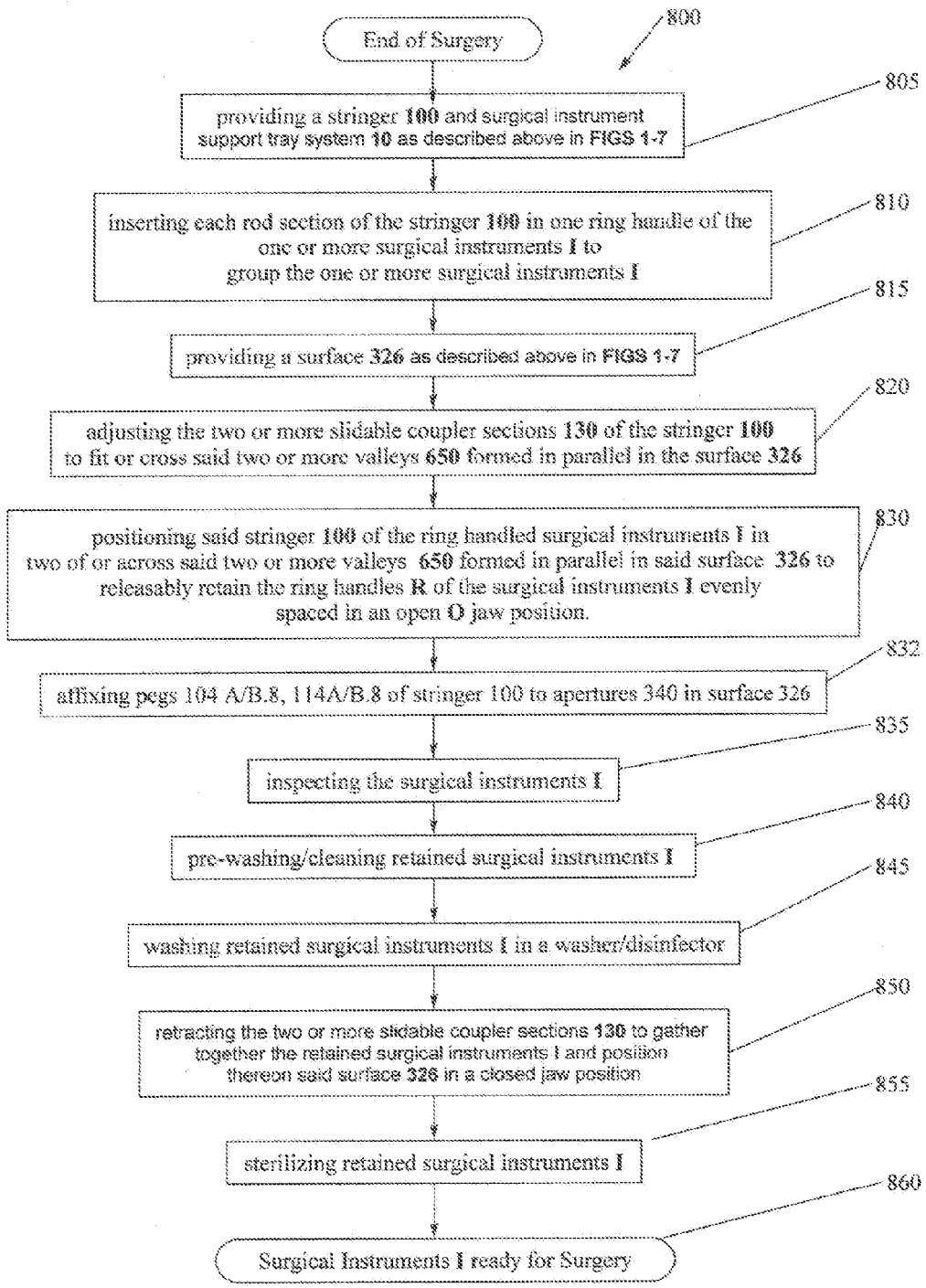
FIG. 8 is a flow diagram of a method of sorting, identifying, grouping, counting, cleaning, pressure washing, sterilizing, and storing surgical instruments prior to surgical use.

Referring to FIG. 8 there is illustrated a flow diagram 800 of a method of organizing, sorting, identifying, grouping, counting, cleaning, pressure washing, sterilizing, and storing prior to surgical use with decreased damage to surgical instruments, and decreased assembly time for sterile surgical instrument sets utilizing, in step 805, providing stringer 100/100A and surgical instrument support tray system 10, shown in FIGS. 1-7.

In block or step 810 and as described above in FIGS. 1-7, upon completion of surgery the operating personnel break down the surgical case and the surgical instruments I are sorted and stringer 100/A rods, such as rods 101A/102A and 101B/102B may be inserted in ring handles R of surgical instruments I to group the set of surgical instruments I by stringing a row of ring handles R of surgical instruments I or by the procedure above for stringer attachment device 700 or attachment devices 801. The grouped set of surgical instruments I may be positioned in valleys 650, step 815 and 830, by adjusting stringer 100/A wherein the surgical instruments I may be identified, counted, sorted and positioned in an organized, parallel relationship in valleys 650 to form a set or group of surgical instruments I. While surgical instruments I have been retained, even spaced with open jaw by stringer 100/A and surgical instrument support tray system 10 an assembler may quickly inspect, identify, sort, count, disengage any of the surgical instruments I for further inspection and operational testing, and grouping of surgical instruments I (inspecting step 835). Thus, surgical instrument support tray system 10 reduces the time spent cleaning, sorting, counting, identifying and grouping surgical instruments I, extends the life expectancy of the surgical instruments, and enables thorough cleaning of the surgical instruments.

In block or step 820, surgical instruments I may be gathered together on one end of stringer 100, stringer 100 may be contracted or adjusted, and laid as a group of surgical instruments I on bottom 226 of tray bottom 220 and tray top 320 may be positioned on tray bottom 220 wherein the basket-like housing or enclosure maintains surgical instruments I in an organized and secure position for sterilization, transportation and storage for later use.

In block or step 830, the grouped set of surgical instruments I may be removed from tray bottom 220 and the grouped set of surgical instruments I may be positioned in or across valleys 650 on tray top 320 by adjusting stringer 100 wherein the surgical instruments I may be retained in parallel or nonparallel, evenly spaced and an open jaw position by surgical instrument support tray system 10. In such position, the grouped set of surgical instruments I may be sprayed and evenly coated with an enzymatic to begin breaking down post-surgery contaminants (pre-washing step 840).

In block or step 832, the grouped set of surgical instruments I may be positioned in or across valleys 650 on tray top 320 by adjusting stringer 100A wherein the surgical instruments I may be retained in parallel or nonparallel, evenly spaced and an open jaw position by surgical instrument support tray system 10 by releasably affixing or inserting pegs 104A/B.8/114A/B.8 to or in apertures 340/340A of tray top 320, and configured to accommodate shorter shanked surgical instrument sets IA and longer shanked surgical instrument sets IB, on one stringer 100A in wide open position O for better cleaning and sterilization purposes and to enable easy identification, pressure washing, sorting, counting, and grouping of surgical instruments IA/B.

In block or step 840, the grouped surgical instruments I and stringer 100 may be pre-washed by submerging into a detergent pre-wash solution or sonification system. In addition, grouped surgical instruments I may be positioned in valleys 650 (step 830) on tray top 320 by adjusting stringer 100 (step 820) wherein the surgical instruments I may be scrubbed or pressure washed to remove any visible contaminants remaining post-surgery and inspected for completeness (pre-washing step 840).

In block or step 850, surgical instruments I may be gathered together on one end of stringer 100, stringer 100 may be contracted or retracted (step 850) with retained parallel spaced and open jaw surgical instruments I, and/or laid as a group of surgical instruments I on bottom 226 of tray bottom 220 and tray top 320 may be positioned on tray bottom 220 wherein the grouped surgical instruments I or basket-like housing or enclosure with surgical instruments I in an organized and secure position and open jaw surgical may be washed in a commercial washer/disinfector (step 845). Since surgical instruments I are retained in parallel, evenly spaced and in an open jaw position this enables even access of detergents and uniform cleaning of surgical instruments I by a commercial washer/disinfector.

In block or step 830, the grouped set of surgical instruments I may be removed from tray bottom 220 and the grouped set of surgical instruments I may be positioned in or across valleys 650 on tray top 320 by adjusting stringer 100 wherein the surgical instruments I may be retained in parallel, evenly spaced and an open jaw position by surgical instrument support tray system 10. While retained an assembler inspects, identifies, sorts and counts surgical instruments I (step 835). Since surgical instruments I have been previously retained in parallel, even spaced with open jaw on surgical instrument support tray system 10 an assembler may quickly inspect, identify, sort, count, disengage any of the surgical instruments I for further inspection and operational testing, and finally grouping of surgical instruments I. Moreover, if one or more surgical instruments I is to be removed or added to the bundled or retained set of surgical instruments I the procedure outlined above for stringer attachment device 700 or alternate stringer attachment devices 800 may be utilized to add or remove surgical instruments I. Thus, surgical instrument support tray system 10 and stringer 100/A reduces the time spent cleaning, sorting, counting, identifying and grouping surgical instruments I, extends the life expectancy of the surgical instruments, and enables thorough cleaning and decontamination of the surgical instruments.

In addition, surgical instrument support tray system and stringer 100/A preferably reduces the number of sharps being bundled or hidden with the surgical instruments I and being sent to sterile central.

In block or step 820 and 850, surgical instruments I may be gathered together on one end of stringer 100/A, stringer 100/A may be contracted with retained parallel spaced and closed jaw surgical instruments I, and laid as a group of surgical instruments I on bottom 226 of tray bottom 220 and tray top 320 and may be positioned on tray bottom 220 wherein the grouped surgical instruments I or basket-like housing or enclosure with surgical instruments I in an organized and secure position and open jaw surgical may be wrapped, containerized (placed in a sterilization container, such as a basket with detachable lid) or stacked for sterile processing/distribution. Surgical instrument support tray(s) system 10 with stringer 100/A retained parallel spaced and open jaw surgical instruments I may be sterilized (step 855) in a commercial sterilizer using steam or other sterilant. The sterilant may access surgical instruments I via a plurality or set of holes such as apertures 240/340/440 in surgical instrument support tray system 10 to enable thorough cleaning and sterilization of surgical instruments. Once sterilized, surgical instrument support tray(s) system 10 with stringer 100 retained parallel spaced and open jaw surgical instruments I may be placed in inventory for future surgical use (step 860).

The foregoing description and drawings comprise illustrative embodiments of the present invention. Having thus described exemplary embodiments, it should be noted by those ordinarily skilled in the art that the within disclosures are exemplary only, and that various other alternatives, adaptations, and modifications may be made within the scope of the present invention. Merely listing or numbering the steps of a method in a certain order does not constitute any limitation on the order of the steps of that method. Many modifications and other embodiments of the invention will come to mind to one ordinarily skilled in the art to which this invention pertains having the benefit of the teachings presented in the foregoing descriptions and the associated drawings. Although specific terms may be employed herein, they are used in a generic and descriptive sense only and not for purposes of limitation. Moreover, the present invention having been described in detail, it should be understood that various changes, substitutions and alterations can be made thereto without departing from the spirit and scope of the invention as defined by the appended claims. Accordingly, the present invention is not limited to the specific embodiments illustrated herein, but is limited only by the following claims.

Therefore, at least the following is claimed:

1. An adjustable stringer configured to string one or more surgical instruments having a first ring handle and a second ring handle, said stringer comprising:
    two or more rod sections, wherein a first rod section is configured to be inserted in the first ring handle of the one or more surgical instruments and a second rod section is configured to be inserted in the second ring handle of the one or more surgical instruments;
    two or more angle sections, each said angle section configured having one or more slidable connector sections, each said one or more slidable connector section configured to extend and retract along at least one of said two or more rod sections; and
   two or more releasable connectors, each said releasable connector positioned between two of said two or more angle sections.

2. The adjustable stringer of claim 1, wherein said one or more slidable connector sections are configured as adjustable in a first axis.

3. The adjustable stringer of claim 2, wherein said two or more releasable connectors are configured to release in a second axis.

4. The adjustable stringer of claim 3, wherein said one or more slidable connector sections and said two or more releasable connectors are configured as adjustable in one of said first axis and said second axis.

5. The adjustable stringer of claim 3, wherein said one or more slidable connector sections and said two or more releasable connectors are configured as rectangular.

6. The adjustable stringer of claim 3, wherein said one or more slidable connector sections and said two or more releasable connectors are configured as trapezium.

7. The adjustable stringer of claim 3, wherein said one or more slidable connector sections and said two or more releasable connectors are configured as trapezoid.

8. The adjustable stringer of claim 1, wherein at least one of said two or more angle sections further comprises a peg.

9. The adjustable stringer of claim 8, wherein said peg is positioned perpendicular to said at least one of said two or more angle sections.

10. A method of organizing one or more surgical instruments having a pair of ring handles, the pair of ring handles includes a first ring handle and a second ring handle, comprising the steps of:
  providing a stringer having two or more rod sections, two or more angle sections, each said angle section configured having one or more slidable connector sections, each of said one or more slidable connector section configured to extend and retract along at least one of said two or more rod sections, each said angel section further configured having at least one peg, and two or more releasable connectors, each said releasable connector positioned between two of said two or more angle sections;
  inserting a first rod section of said two or more rod sections in the first ring handle of the one or more surgical instruments and a second rod section of said two or more rod sections in the second ring handle of the one or more surgical instruments;
  providing a surface configured to support the one or more surgical instruments, said surface further comprises a plurality of holes configured to enable sterilant to flow therethrough;
  adjusting said two or more slidable connector sections of said stringer to position said peg adjacent one of said plurality of holes; and
  positioning said at least one peg in one of said plurality of holes to releasably retain the ring handles of the surgical instruments evenly spaced in an open jaw position.

11. The method of claim 10, further comprises the step of inspecting the surgical instruments.

12. The method of claim 10, further comprises the step of pre-washing the surgical instruments.

13. The method of claim 10, further comprises the step of washing the surgical instruments.

14. The method of claim 10, further comprises the step of retracting said two or more slidable connector sections to group together the pair of ring handles of the surgical instruments and position the surgical instruments thereon said surface with the surgical instruments in an open jaw position.

15. The method of claim 10, further comprises the step of sterilizing the surgical instruments in said open jaw position.

16. The method of claim 10, reducing a time increment to clean the surgical instruments.

17. The method of claim 10, reducing a number of sharps bundled with the surgical instruments.

* * * * *